(12) United States Patent
Umberger et al.

(10) Patent No.: US 12,127,860 B2
(45) Date of Patent: Oct. 29, 2024

(54) WEARABLE DEVICE NETWORK SYSTEM

(71) Applicant: WEST AFFUM HOLDINGS DAC, Dublin (IE)

(72) Inventors: Traci S. Umberger, Kirkland, WA (US); Brian D. Webster, Mercer Island, WA (US); Phillip D. Foshee, Jr., Woodinville, WA (US); Gordon P. Teddy, Maple Valley, WA (US); Krystyna Szul, Seattle, WA (US)

(73) Assignee: WEST AFFUM HOLDINGS DAC, Dublin (IE)

( * ) Notice: Subject to any disclaimer, the term of this patent is extended or adjusted under 35 U.S.C. 154(b) by 415 days.

(21) Appl. No.: 17/518,573

(22) Filed: Nov. 3, 2021

(65) Prior Publication Data

US 2022/0225949 A1 Jul. 21, 2022

Related U.S. Application Data

(60) Provisional application No. 63/139,957, filed on Jan. 21, 2021.

(51) Int. Cl.
*A61B 5/00* (2006.01)
*A61B 5/024* (2006.01)
*G06F 21/62* (2013.01)
*G16H 10/60* (2018.01)
*G16H 40/67* (2018.01)
(Continued)

(52) U.S. Cl.
CPC .......... *A61B 5/747* (2013.01); *A61B 5/02438* (2013.01); *A61B 5/725* (2013.01); *A61B 5/7264* (2013.01); *A61B 5/746* (2013.01); *A61B 5/749* (2013.01); *G06F 21/6254* (2013.01); *G16H 10/60* (2018.01); *G16H 40/67* (2018.01); *G16H 50/30* (2018.01); *A61N 1/3904* (2017.08); *A61N 1/3925* (2013.01)

(58) Field of Classification Search
CPC ............................... G16H 40/67; G16H 10/60
USPC ........................................................ 600/508
See application file for complete search history.

(56) References Cited

U.S. PATENT DOCUMENTS

| | | |
|---|---|---|
| 3,724,455 A | 4/1973 | Unger |
| 4,583,524 A | 4/1986 | Hutchins |
| 4,619,265 A | 10/1986 | Morgan et al. |

(Continued)

FOREIGN PATENT DOCUMENTS

WO 1998039061 A2 9/1998

OTHER PUBLICATIONS

Pagan-Carlo, et al., "Encircling Overlapping Multipulse Shock Waveforms for Transthoracic Defibrillation," JACC Journals, Dec. 1998, vol. 32 Issue 7, p. 2065-2071.

(Continued)

*Primary Examiner* — Nadia A Mahmood
(74) *Attorney, Agent, or Firm* — Polsinelli PC

(57) ABSTRACT

In one embodiment, a method to track cardiac health of a patient is described. The method includes communicating, via a mobile device, to a cardiac device worn by the patient, wherein the cardiac device includes at least one sensor. The method also includes receiving cardiac device data from the cardiac device and filtering the cardiac device data based at least in part on patient logic rules. The method includes pushing the cardiac device data to one or more personnel based at least in part on the patient logic rules.

19 Claims, 13 Drawing Sheets

(51) Int. Cl.
*G16H 50/30* (2018.01)
*A61N 1/39* (2006.01)

(56) References Cited

U.S. PATENT DOCUMENTS

| | | | |
|---|---|---|---|
| 4,928,690 A | 5/1990 | Heilman et al. |
| 4,955,381 A | 9/1990 | Way et al. |
| 5,078,134 A | 1/1992 | Heilman et al. |
| 5,228,449 A | 7/1993 | Christ et al. |
| 5,348,008 A | 9/1994 | Bornn et al. |
| 5,353,793 A | 10/1994 | Bornn |
| RE34,800 E | 11/1994 | Hutchins |
| 5,394,892 A | 3/1995 | Kenny |
| 5,405,362 A | 4/1995 | Kramer et al. |
| 5,474,574 A | 12/1995 | Payne et al. |
| 5,662,690 A | 9/1997 | Cole et al. |
| 5,782,878 A | 7/1998 | Morgan et al. |
| 5,792,204 A | 8/1998 | Snell |
| 5,902,249 A | 5/1999 | Yster |
| 5,913,685 A | 6/1999 | Hutchins |
| 5,944,669 A | 8/1999 | Kaib |
| 6,047,203 A | 4/2000 | Sackner et al. |
| 6,065,154 A | 5/2000 | Hulings et al. |
| 6,108,197 A | 8/2000 | Janik |
| 6,148,233 A | 11/2000 | Owen et al. |
| 6,201,992 B1 | 3/2001 | Freeman |
| 6,263,238 B1 | 7/2001 | Brewer et al. |
| 6,287,328 B1 | 9/2001 | Snyder et al. |
| 6,304,780 B1 | 10/2001 | Owen et al. |
| 6,319,011 B1 | 11/2001 | Motti et al. |
| 6,334,070 B1 | 12/2001 | Nova et al. |
| 6,356,785 B1 | 3/2002 | Snyder |
| 6,427,083 B1 | 7/2002 | Owen et al. |
| 6,437,083 B1 | 7/2002 | Owen et al. |
| 6,529,875 B1 | 3/2003 | Nakajima |
| 6,546,285 B1 | 4/2003 | Owen et al. |
| 6,671,545 B2 | 12/2003 | Fincke |
| 6,681,003 B2 | 1/2004 | Linder et al. |
| 6,762,917 B1 | 7/2004 | Verbiest et al. |
| 7,065,401 B2 | 6/2006 | Worden |
| 7,559,902 B2 | 7/2009 | Ting et al. |
| 7,865,238 B2 | 1/2011 | Brink |
| 7,870,761 B2 | 1/2011 | Valentine et al. |
| 7,974,689 B2 | 7/2011 | Volpe et al. |
| 8,135,462 B2 | 3/2012 | Owen et al. |
| 8,140,154 B2 | 10/2012 | Donnelly et al. |
| 8,369,944 B2 | 2/2013 | Macho et al. |
| 8,548,557 B2 | 10/2013 | Garstka et al. |
| 8,615,295 B2 | 12/2013 | Savage et al. |
| 8,644,925 B2 | 2/2014 | Volpe et al. |
| 8,897,860 B2 | 11/2014 | Volpe et al. |
| 8,904,214 B2 | 12/2014 | Volpe et al. |
| 8,965,500 B2 | 2/2015 | Macho et al. |
| 9,008,801 B2 | 4/2015 | Kaib et al. |
| 9,089,685 B2 | 7/2015 | Sullivan et al. |
| 9,131,901 B2 | 9/2015 | Volpe et al. |
| 9,132,267 B2 | 9/2015 | Kaib |
| 9,408,548 B2 | 8/2016 | Volpe et al. |
| 9,454,219 B2 | 9/2016 | Volpe et al. |
| 9,592,403 B2 | 3/2017 | Sullivan |
| 2003/0158593 A1 | 8/2003 | Heilman et al. |
| 2005/0107833 A1 | 5/2005 | Freeman et al. |
| 2005/0107834 A1 | 5/2005 | Freeman et al. |
| 2008/0312709 A1 | 12/2008 | Volpe et al. |
| 2009/0005827 A1 | 1/2009 | Weintraub et al. |
| 2010/0007413 A1 | 1/2010 | Herleikson |
| 2010/0298899 A1 | 11/2010 | Donnelly et al. |
| 2011/0022105 A9 | 1/2011 | Owen et al. |
| 2011/0288604 A1 | 11/2011 | Kaib et al. |
| 2011/0288605 A1 | 11/2011 | Kaib et al. |
| 2012/0112903 A1 | 5/2012 | Kaib et al. |
| 2012/0144551 A1 | 6/2012 | Guldalian |
| 2012/0150008 A1 | 6/2012 | Kaib et al. |
| 2012/0158075 A1 | 6/2012 | Kaib et al. |
| 2012/0265265 A1 | 10/2012 | Razavi et al. |
| 2012/0283794 A1 | 11/2012 | Kaib et al. |
| 2012/0293323 A1 | 11/2012 | Kaib et al. |
| 2012/0302860 A1 | 11/2012 | Volpe et al. |
| 2012/0310315 A1 | 12/2012 | Savage et al. |
| 2013/0085538 A1 | 4/2013 | Volpe et al. |
| 2013/0231711 A1 | 9/2013 | Kaib |
| 2013/0245388 A1 | 9/2013 | Rafferty et al. |
| 2013/0274565 A1 | 10/2013 | Langer et al. |
| 2013/0317852 A1 | 11/2013 | Worrell et al. |
| 2013/0325078 A1 | 12/2013 | Whiting et al. |
| 2014/0025131 A1 | 1/2014 | Sullivan et al. |
| 2014/0070957 A1 | 3/2014 | Longinotti-Buitoni et al. |
| 2014/0163663 A1 | 6/2014 | Poddar et al. |
| 2014/0324112 A1 | 10/2014 | Macho et al. |
| 2014/0378812 A1 | 12/2014 | Saroka et al. |
| 2015/0039053 A1 | 2/2015 | Kaib et al. |
| 2015/0328472 A1 | 11/2015 | Sullivan et al. |
| 2016/0004831 A1 | 1/2016 | Carlson et al. |
| 2016/0082277 A1 | 3/2016 | Foshee, Jr. et al. |
| 2016/0135706 A1* | 5/2016 | Sullivan .............. A61B 5/4803 600/509 |

OTHER PUBLICATIONS

The LifeVest Network/Patient Data Management System, Zoll, 2015, 2000503 Rev A.

Klein, H. U., Goldenberg I., & Moss, A. J., Risk Stratification for Implantable Cardioverter Defibrillator Therapy: The Role of the Wearable Cardioverter-Defibrillator, Clinical update, European Heart Journal, May 31, 2013, pp. 1-14, doi:10.1093/eurheartj/eht167, European Society of Cardiology.

LIFECOR LifeVest System Model WCD 3100 Operator's Manual, 2006, PN 20B0040 Rev FI, Zoll Lifecor Corporation, Pittsburgh, PA.

LifeVest Model 4000 Patient Manual, Zoll, 2009, PN 20B0047 Rev B.

Heartstart MRx and XL AED Algorithm—Application Note, Jul. 2001, Edition 2 Philips Healthcare, USA.

The LifeVest Network/Patient Data Management System, Zoll, 2015, 20C0503 Rev A.

* cited by examiner

WEARABLE DEVICE NETWORK SYSTEM

CROSS-REFERENCE TO RELATED PATENT APPLICATIONS

This patent application claims the benefit of U.S. Provisional Patent Application No. 63/139,957 filed Jan. 21, 2021, and is incorporated herein by reference in their entirety for all purposes.

BACKGROUND

When people suffer from some types of heart arrhythmias, in some instances, blood flow to various parts of the body may be reduced. Some arrhythmias can result in a Sudden Cardiac Arrest (SCA). SCA can lead to death quickly, e.g., within 10 minutes, unless treated in the interim. Some observers have thought that SCA is the same as a heart attack, which it is not.

Some people have an increased risk of SCA. Such people may include patients who have had a heart attack or a prior SCA episode. A frequent recommendation for these people is to receive an Implantable Cardioverter Defibrillator (ICD). The ICD is surgically implanted in the chest and continuously monitors the patient's intracardiac electrogram (IEGM). If certain heart arrhythmias are detected, the ICD delivers an electric shock through the heart.

As a further precaution, people who have been identified to have an increased risk of SCA are sometimes given a Wearable Cardioverter Defibrillator (WCD) system to wear until an ICD is implanted. Early versions of such systems were called wearable cardiac defibrillator systems. A WCD system typically includes a harness, vest, belt, or another garment that the patient wears. The WCD system further includes electronic components, such as a defibrillator and electrodes, coupled to the harness, vest, or another garment. When the patient wears the WCD system, the electrodes may electrically contact the patient's skin and aid in sensing the patient's electrocardiogram (ECG). If a shockable heart arrhythmia (e.g., ventricular fibrillation or VF) is detected from the ECG, the defibrillator delivers an appropriate electric shock through the patient's body, and thus through the heart. The delivered shock may restart the patient's heart and save the patient's life.

BRIEF SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

The present disclosure describes instances and examples of cardiac monitoring systems (e.g., WCD systems), devices, systems, storage media that may store programs and methods.

In one embodiment, a method to track cardiac health of a patient is described. The method includes communicating, via a mobile device, to a cardiac device worn by the patient, wherein the cardiac device includes at least one sensor. The method also includes receiving cardiac device data from the cardiac device and filtering the cardiac device data based at least in part on patient logic rules. The method includes pushing the cardiac device data to one or more personnel based at least in part on the patient logic rules.

In some embodiments, the method may include issuing a notification to one or more personnel. In some embodiments, the method may include detecting a voice command, interpreting the voice command, and taking one or more actions concerning the cardiac device based at least in part on the voice command.

In some embodiments, the cardiac device may be a wearable cardiac defibrillator. In some embodiments, the method may include mirroring the cardiac device data on a second device remote from the first device, wherein the second device is associated with professional personnel. The data may have been filtered and approved for the professional personnel.

In some embodiments, the method may include receiving a message from the professional personnel and displaying the message to the patient. In another embodiment, a method to track cardiac health of a patient is described. The method includes establishing communication with a mobile device coupled to a cardiac device proximate a patient, wherein the cardiac device includes at least one sensor. The method includes receiving cardiac device data from the mobile device and filtering the cardiac device data based at least in part on patient logic rules. The method also includes pushing the cardiac device data to one or more personnel based at least in part on the patient logic rules.

In some embodiments, the method may include issuing a notification to one or more health care personnel, wherein the notification includes a health alert about the patient. In some embodiments, the method may include transferring patient health data and identification information to one or more health care personnel based at least in part on the patient logic rules. The cardiac device may be a wearable cardiac defibrillator. In some embodiments, the method may include removing patient identifying information from patient health data and transferring anonymous patient health data to one or more providers of the cardiac device based at least in part on the patient logic rules. In some embodiments, the method may include removing patient identifying information from patient health data and device data and transferring anonymous patient health data and device data to one or more customer service personnel based at least in part on the patient logic rules. The patient logic rules may include at least one of a care station logic module, a medical logic module, a customer service logic module, and a customer relationship management (CRM) logic module.

In some embodiments, the care station logic module may filter data for storage at a centralized location. The care station may be a centralized storage database that runs patient logic rules. In some embodiments, the medical logic module may filter data for transferring to medical personnel. The customer service logic module may filter device data for customer service personnel. The CRM logic module may filter patient data for CRM personnel.

In another embodiment, a system for monitoring the health of a patient is described. The system includes a sensing device configured to be worn by a patient and at least one camera in communication with the sensing device, the at least one camera configured to automatically activate when the sensing device detects a triggering event and the at least one camera upon activation sends at least one image to a remote location.

In some embodiments, the triggering event may include at least one of a sensed motion of a patient or a sensed physiological parameter of the patient. In some embodiments, the sensing device may be a wearable cardiac defibrillator. In some embodiments, the sensing device may be a wearable monitoring device. In some embodiments, the camera may be part of a home security system. In some embodiments, the at least one camera may include a microphone and a speaker. In some embodiments, the camera may capture video and sound. In some embodiments, the camera may transmit the voice of a third party to the patient.

In another embodiment, method for monitoring a status of a patient is described. The method includes receiving, automatically, a notification of a cardiac event from a wearable device and determining a location of the wearable device based at least in part on the notification. The method includes focusing a camera lens on the wearable device, wherein the lens captures the entirety of the patient and recording, via the camera device, video and audio of the patient for a predetermined time period. The method also includes transmitting, automatically, the video and audio data to a third party.

In some embodiments, the method may include analyzing the video and audio data for patient status. In some embodiments, the method may include activating a speaker proximate the camera and distributing information to the patient via the speaker. In some embodiments, the method may include detecting a bystander proximate the patient, activating a speaker proximate the camera, and issuing commands to the bystander via the speaker. In some embodiments, the commands may include informational prompts to request data form the bystander. In some embodiments, the method may include automatically navigating the camera from a base location to the patient's location.

In some embodiments, the method may include issuing a prompt to the patient requesting patient feedback via a wearable device, receiving a response from the patient, and cancelling the emergency event and deactivating the cameras. In some embodiments, the method may include issuing a prompt to the patient requesting patient feedback via a wearable device, waiting a predetermined time period after issuing the prompt, and contacting emergency personnel when a response is not received within the predetermined time period.

BRIEF DESCRIPTION OF THE DRAWINGS

The foregoing aspects and many of the attendant advantages of this disclosure will become more readily appreciated as the same become better understood by reference to the following detailed description, when taken in conjunction with the accompanying drawings, wherein.

DETAILED DESCRIPTION

Figure 1:
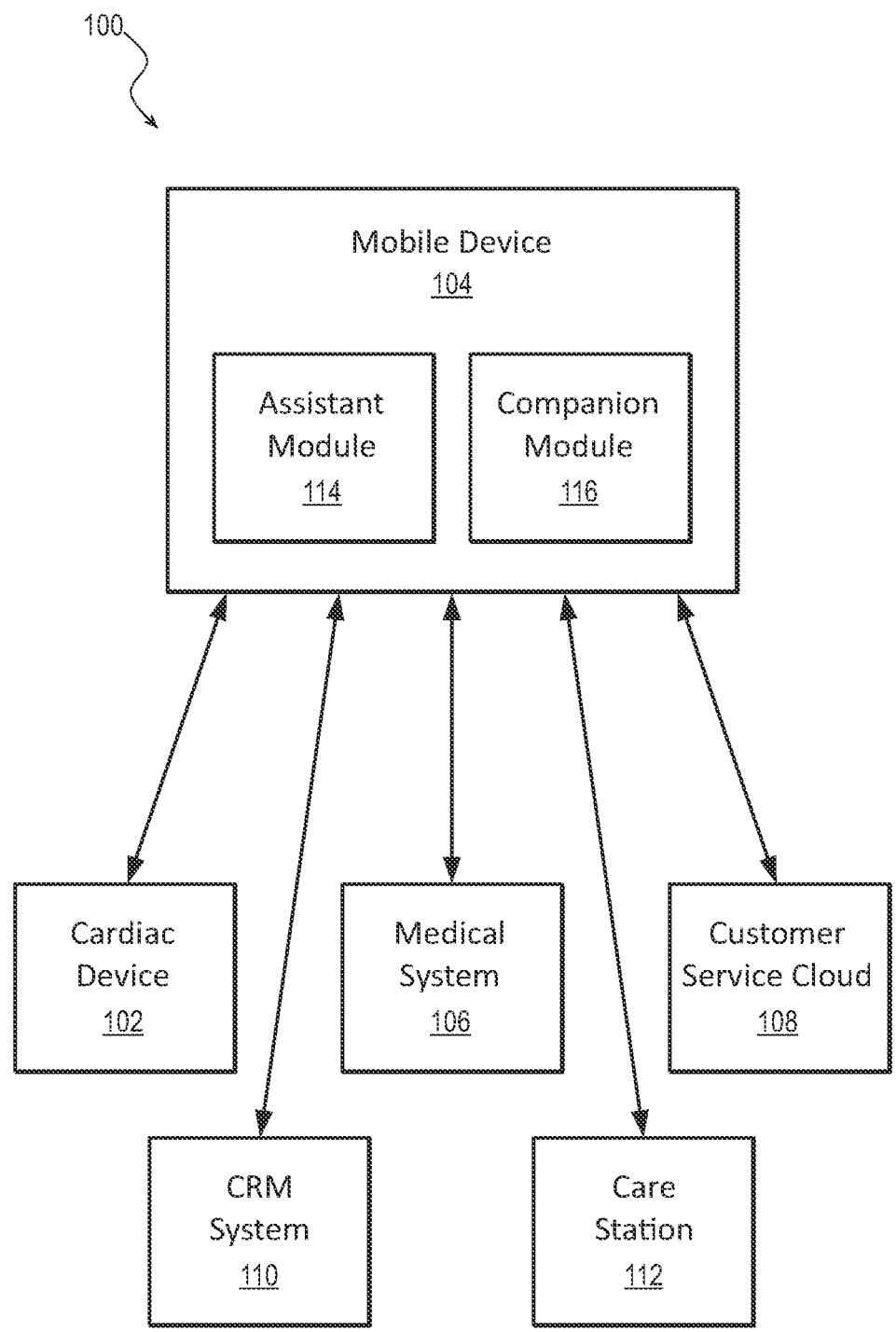
FIG. 1 is a diagram of a sample wearable device system in accordance with exemplary embodiments described herein.

The detailed description set forth below in connection with the appended drawings, where like numerals reference like elements, are intended as a description of various embodiments of the present disclosure and are not intended to represent the only embodiments. Each embodiment described in this disclosure is provided merely as an example or illustration and should not be construed as precluding other embodiments. The illustrative examples provided herein are not intended to be exhaustive or to limit the disclosure to the precise forms disclosed.

In the following description, specific details are set forth to provide a thorough understanding of exemplary embodiments of the present disclosure. It will be apparent to one skilled in the art, however, that the embodiments disclosed herein may be practiced without embodying all of the specific details. In some instances, well-known process steps have not been described in detail in order not to unnecessarily obscure various aspects of the present disclosure. Further, it will be appreciated that embodiments of the present disclosure may employ any combination of features described herein.

The present description includes examples of cardiac monitoring and treatment systems, such as a Wearable Cardiac Defibrillator (WCD) system and other wearable cardiac monitoring devices, as well as alert management systems and methods. The disclosure will discuss a WCD and provide examples using a WCD, but it will be understood that other systems can be used instead of a WCD.

Embodiments of wearable health monitoring systems include wearable ECG monitors, wearable vital sign monitoring systems, including temperature, blood pressure monitors, heart rate monitors, SPO2 detectors, step detectors, infusion pumps, etc. In some scenarios, such systems can be utilized alone or in combination with other devices, systems, or both. Furthermore, such devices, systems, or both can be supported by accessories, which can assist with data collection, transfer, trending as well as alerts. Such accessories can include tablets, mobile devices such as a cell phone or a watch.

Patients wearing WCDs may experience issues requiring a response from medical personnel, customer service, or from CRM personnel. Alternatively, in some scenarios, a doctor, customer service representative, or CRM personnel may want to check the status of a patient, engage and interact with the patient to encourage compliance and wellness, and confirm wellness with the patient and WCD. To date, no publicly available systems provide this level interaction with these varied groups of personnel.

WCD systems according to some embodiments of the present disclosure can advantageously enable information from the to be communicated to medical personnel, customer service, CRM system, or some combination thereof so that they can easily access the information provided by the WCD and in response take appropriate actions.

For example, the WCD system may communicate with a mobile device. The mobile device may be equipped with modules which enable communication information to the medical personnel, customer service, CRM system, or some combination thereof. These various personnel can use this information to take appropriate actions that can benefit the patient, increase efficiency in providing services to and receiving requests from the patient, and improve the operation the WCD system.

FIG. 1 illustrates a block diagram of a cardiac device monitoring system 100 according to one embodiment described herein. The monitoring system 100 includes a cardiac device 102 in communication with a mobile device 104. The mobile device 104 is also in communication with one or more medical personnel or medical entities 106, a customer service cloud 108, a customer relationship management (CRM) system 110, and a Care Station 112.

Figure 6:
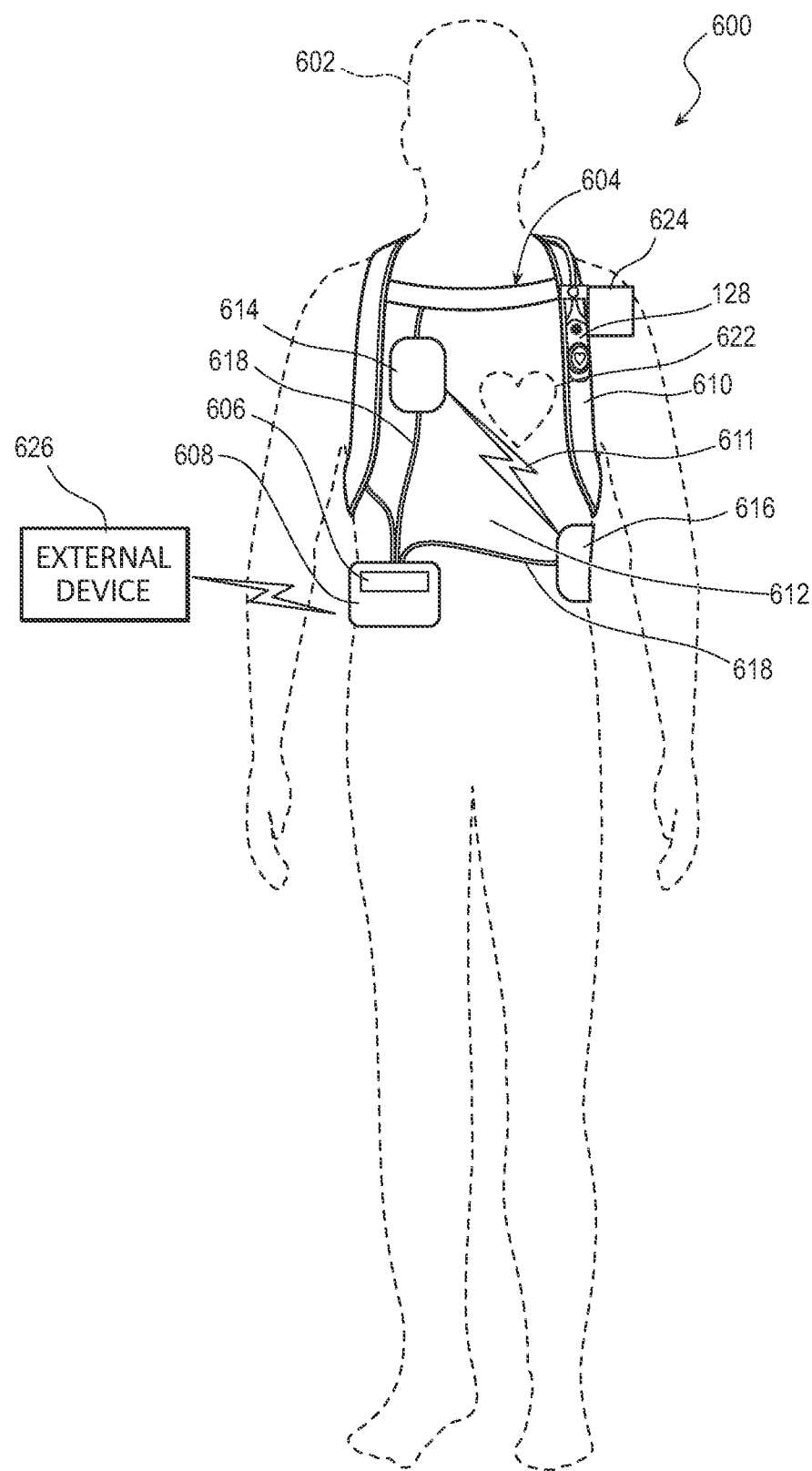
FIG. 6 is a diagram of a sample wearable device system in accordance with exemplary embodiments described herein

The cardiac device 102 may include a WCD as described in reference to FIG. 6. In some embodiments, the cardiac device 102 may also include other wearable health monitoring systems described herein. In some embodiments, the cardiac device 102 may include a wearable medical grade monitoring device. The cardiac device 102 may have a graphical user interface (GUI) and a wireless communication module, among other features.

The mobile device 104 may be a smartphone commercially available to the public, a dedicated or customized communication device, a smartwatch, a tablet, or the like. In some embodiments, the mobile device 104 may be a specific device unique to the cardiac device 102. For example, the mobile device 104 may be a unique device separate from a personal device that may couple with the cardiac device 102 and track patient health and device status. In some embodiments, the mobile device 104 may wirelessly communicate with the cardiac device 102 to receive cardiac and other health information such as movement data, respiration data, sleeping data, and the like. For example, the wireless device 104 may couple to the cardiac device via Bluetooth, WiFi, or other wireless connectivity methods.

In some embodiments, the mobile device 104 may also include a voice activation and control module. The voice activation and control module may be similar to the systems used in Apple® or Android® devices. The voice activation may enable the patient to communicate with a device using their voice. There may be a wake word the patient uses. In some embodiments, the wake word may be specific to the particular device brand. In other embodiments, the mobile device 104 may be activated with a word or phrase specific to the cardiac device 102. This may alert the mobile device 104 of the need to activate a patient portal or other application proximate the mobile device 104. In some embodiments, the patient may further command the mobile device 104 to take one or more actions. The actions may direct the impact of the cardiac device 102, such as dismissing or snoozing an alarm. In emergency situations, the mobile device 104 may respond to voice activation and commands to contact emergency personnel.

The care station 112 is a remote server able to communicate with the mobile device 104. In some embodiments, the care station 112 may have a module or interface which may securely receive and store information from the cardiac device 102 via the mobile device 104. In some embodiments, the care station 112 may be in direct communication with the cardiac device 102. The care station 112 may securely store all patient data relating to the cardiac device 102.

The medical system 106 may be a medical system linked to a patient's physician, or other attending doctor. The medical system 106 may grant access to a cardiologist, an assistant, a nurse, a primary care doctor, or the like. In some embodiments, the medical system 106 may additionally be authorized personnel able to receive information for medical studies or other research projects. The medical personnel may interface with the mobile device 104 via their own mobile devices, personal computers, or the like. In some embodiments, the medical personnel may interface with the medical system 106 using their own servers and systems which may then grant access to the appropriate medical personnel.

The Customer Service Cloud 108 may be a remote cloud server which may receive data from the mobile device 104. The customer service cloud 108 may be operated by the company who provided the cardiac device 102. The customer service personnel may use the cloud 108 to monitor the data received from the cardiac device 102 to ensure proper communications. The customer service may assist the patient with operating the WCD, troubleshooting problems, answering questions from the patient, etc.

The CRM system 110 may be a technology which may manage the company's relationships and interactions with customers and potential customers. In some embodiments, the CRM 110 system may grant access to operators of a software tools/databases to manage and track information about inventory of cardiac devices 102 and system components, patients, prevention status reports (PSRs), and cardiac device prescriptions.

In some embodiments, the CRM system 110 may be analytical. For example, the CRM system 110 may analyze customer data collected from multiple cardiac devices 102. The CRM system 110 may use techniques such as data mining, correlation, and pattern recognition to analyze the customer data. The CRM system 110 may enable the customer team to provide support to the clients.

In the embodiment shown in FIG. 1, the mobile device 104 has an assistant module 114 and a companion module 116. The assistant module 114 runs on the mobile device 104 and may communicate information between the cardiac device 104 and the care station 112. In some embodiments, the assistant module 114 may alter the functionality of the cardiac device 104. For example, the patient may use the assistant module 114 to check a status of cardiac device 102, this may include silencing alarms, checking battery status, providing input, and the like. The assistant module 114 may also provide heart rate information which may enable the patient to determine their cardiac status. The assistant module 114 may also enable the patient to communicate with the various entities required. For example, the patient may communicate with their medical team through the assistant module 102 and medical system 106. The patient may also be able to request support from the customer service team, the CRM team, or the like.

The companion module 116 may work in conjunction with the assistant module 114. For example, the companion module 116 may communicate with the medical system 106, the customer service cloud 108, and the CRM system 110 to facilitate interactions with the patient, improve efficiencies in responding to patient needs and managing/tracking resources (including service personnel) used in and by the cardiac system 102. In some embodiments, the companion module 116 may communicate with the care station 112 either directly or via the assistant module 114. In some embodiments, the companion module 116 may be implemented as disclosed U.S. Prov. App. No. 63/069,627 filed Aug. 24, 2020, entitled "Health and Emotional Support Companion" to interact with the patient. U.S. Prov. App. No. 63/069,627 is incorporated herein in its entirety for all purposes. The companion module 116 may work to share data and information whereas the assistant module 114 may interface with the patient.

In some embodiments, the companion module 116 may push notifications to the medical system 106, customer service cloud 108, or the CRM system 110. This may enable the proper counterpart (i.e., a doctor, customer service representative, technical support personnel, and the like) to receive notifications and properly respond. In some embodiments, the companion module 116 may filter notifications through an algorithm to determine which personnel should be receiving which notifications. This may enable the proper personnel to appropriately respond to the notification. For example, a medical doctor may not be able to troubleshoot a cardiac device 102 hardware issue, but a technical support representative cannot review an irregular heartbeat to prescribe medical care. By filtering information, the medical and personal information maintains a level of protection and privacy.

In some embodiments, the assistant module 114 and the companion module 116 may integrated into a single module. A single interface may present a simpler interface for a patient. A single module may improve efficiency and decrease the power consumption and processor resource usage of the mobile device 104.

Figure 2:
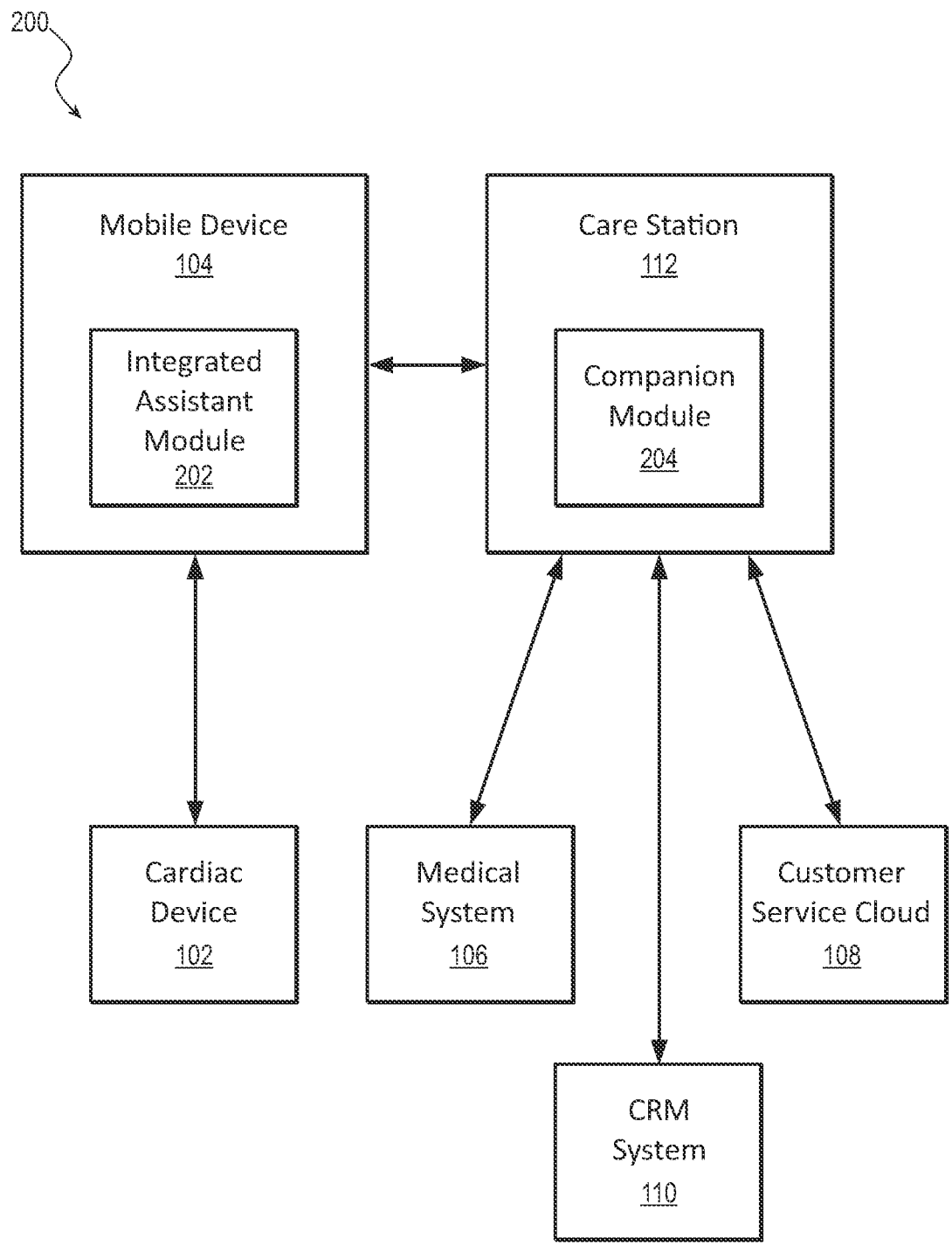
FIG. 2 is a diagram of a sample wearable device system in accordance with exemplary embodiments described herein.

FIG. 2 illustrates a block diagram of a cardiac device system 200 according to an alternative embodiment. The cardiac device system 200 includes at least one cardiac device 102, a respective mobile device 104. In contrast to the system 100 described with reference to FIG. 1, the system 200 shown in FIG. 2 displays the care station 112 as an intermediary between the mobile device 104 and the medical system 106, customer service cloud 108, and the CRM system.

In the embodiment shown in FIG. 2, the mobile device has an integrated assistant module 202. As mentioned previously, the integrated assistant module 202 may combine the abilities of the assistant module 114 and the companion module 116. In some embodiments, the integrated assistant module 202 may solely interface with and communicate with the care station 112.

In this system 200, the care station 112 securely communicates with the other components of the cardiac health device system 200. The care station 112 may insulate or secure the patient and their mobile device 104 from the other components of the system. The extra layer of security may increase patient privacy by allowing the care station 112 to filter and protect the patient's data. Additionally, in some embodiments, the single interface to the care station 112 may improve efficiency of the communications between the patient and the medical systems 106, customer service cloud 108, CRM system 110 and the respective personnel accessing those systems. The care station 112 may also reduce load and power consumption of the mobile device 102. For example, the care station 112 may perform processing and communications performed by the mobile device 102 shown in FIG. 1.

In some embodiments, the medical system 106, customer service cloud 108, and CRM system 110 may have a module that mirrors the integrated assistant module 202. For example, the systems 106, 108, 110 may have a mirror assistant module. In some embodiments, the information displayed by and accessible via the integrated assistant module 202 may be transmitted or otherwise reproduced by the various mirror assistant modules. Each respective mirror assistant module may be controlled to restrict access to information appropriate for the particular end user. This enables the various personnel to access pertinent data from the integrated assistant module 202 without needing to contact and seek a response from the patient. The data may require responsive actions to benefit the patient, increase efficiency in providing services to and receiving requests from the patient, and improve the operation the cardiac device 102.

Figure 3:
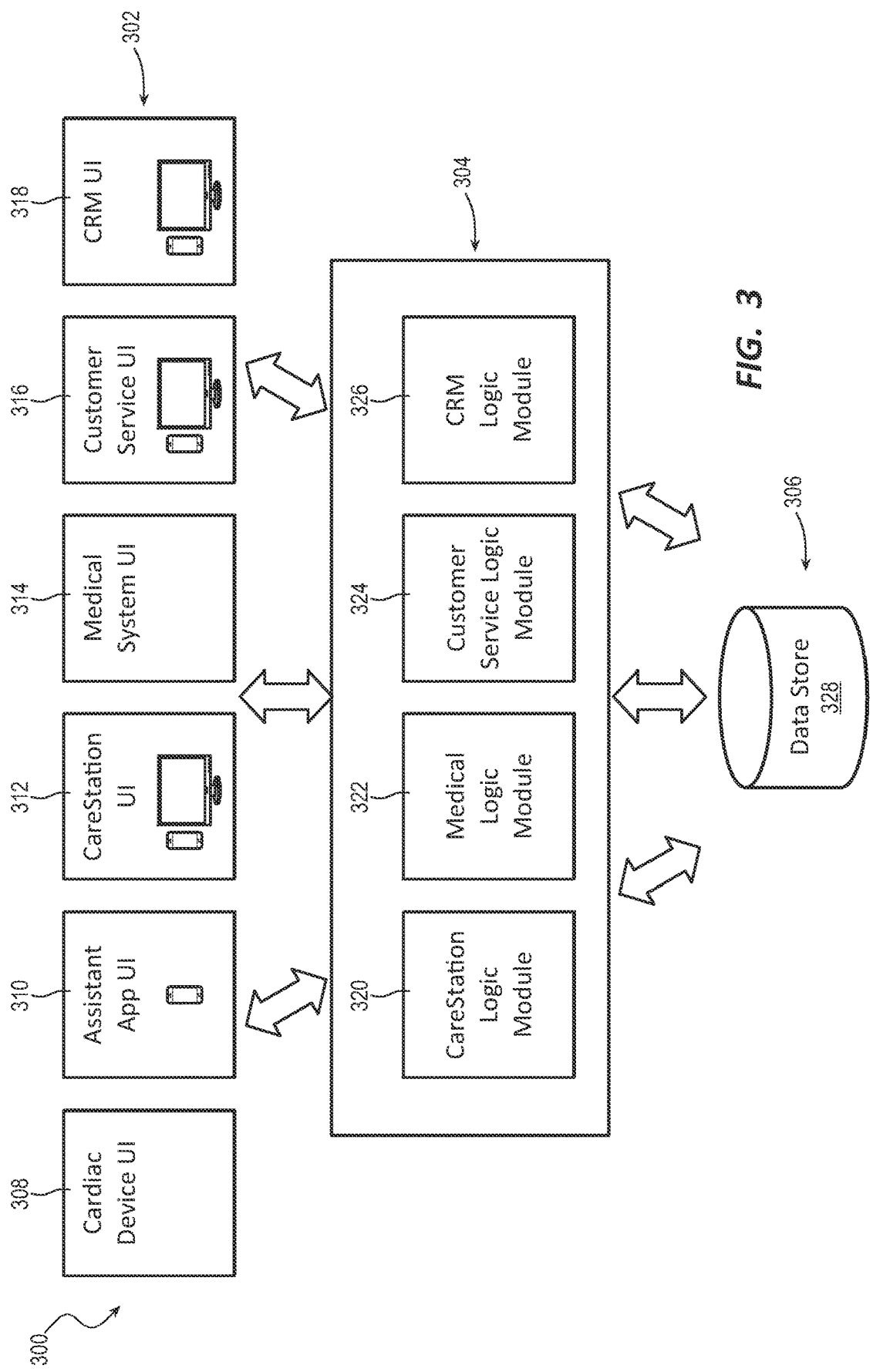

FIG. 3 is an illustration of a layered software architecture 300 according to exemplary embodiments described herein. As show in FIG. 3, the layered software architecture has a presentation layer 302, an integration layer 304, and a data layer 306.

The presentation layer 302 may include a variety of user interfaces. Each separate user interface (UI) may allow the respective party to access a different variation of the cardiac data and cardiac device information. Some examples of UIs include cardiac device UI 308, an assistant module UI 310, a care station UI 312, a medical system UI 314, a customer service UI 316, and a CRM UI 318. The UIs 308, 310, 312, 314, 316, 318 may enable patients and other users to interact with those respective components. Some components may include both mobile devices and desktop type display devices with a respective UI. Each UI 308, 310, 312, 314, 316, 318 may be configured so that only predetermined categories of information for the respective personnel can be communicated with the respective user interface. The user interfaces 308, 310, 312, 314, 316, 318 may be implemented in the presentation layer 302 with one or more common interfaces to the integration layer.

In some embodiments, the integration layer 304 may act as a guardian of patient information. For example, the integration layer 304 may implement data logic to restrict and grant access to portions of a patient's health record. For example, each respective party, medical system 106, customer service cloud 108, and CRM system 110, may be privy to select components of data. The information necessary for a doctor is not the same information required for a customer service personnel. The integration layer 304 may include modules for each party requesting access to the patient's data. In the example shown, the integration layer 304 includes a care station logic module 320, a medical logic module 322, customer service logic module 324, and CRM logic module 326. In further embodiments, the integration layer 304 may include more or less or some varied combination of logic modules.

The care station logic module 320 may run all data logic for care station functions. The care station logic module 320 may control data storage and communication between the patient and the various personnel. The care station logic module 320 may also determine which information is viable and requires long term storage and run all patient data through a Health Insurance Portability and Accountability Act (HIPAA) logic module to ensure all patient data is stored according to federal standards. The care station logic module 320 may also comply with any state and local patient privacy and data standards.

The medical logic module 322 may filter all the data necessary for medical care. For example, the physician does not need to know if the device was plugged in or if there a low battery warning. However, the doctor does need to know the patient data such as heart rate data and the respective patient the data belongs to. Therefore, the medical logic module 322 may filter through all the data from the remote device 104 and provide only medical data to medical professionals. In some embodiments, the medical logic module 322 may contain rules controlling access to certain patient data; processing information for display to a user (e.g., charts, trends, dashboards, and other analytics); storing data in the data layer; and the like.

The customer service logic 324 may filter data necessary for customer service personnel. In some embodiments, this information may include device data, wearability data, and the like. In some embodiments, the customer service personnel may study the heart rate data from patients to improve and troubleshoot readings. However, to protect patient privacy, the data may be scrubbed of any identifying characteristics. If the cardiac device 102 requires technical support, in some instances, the customer service personnel may be able to anonymously send data to the appropriate patient. For example, the customer service logic may anonymize the data to the customer service personnel but still maintain an anonymous identifier to allow the customer service personnel to anonymously reach the patient.

In another embodiment, the integration layer 304 may include a research logic module. The research logic module may provide the medical anonymously to researchers who may study the heart rate data and cardiac device and other patient data.

The CRM logic module 326 may provide information to the organization supplying the cardiac device 102. Therefore, the CRM logic module 326 may provide data to the CRM personnel that allow the customer relationship personnel to investigate issues related to patient data, such as wear time and device alerts.

In some embodiments, the integration layer 304 may run on one or more servers, a web services environment, or some combination thereof. Each of the modules present on the integration layer 304 implement logic and processing of information from the presentation layer 302, the data layer 306, or some combination thereof.

In addition, the modules implemented in the integration layer 304 may process data such as form reports, trend data, information access controls, and the like. In the example cardiac system of FIG. 1, the care station may be a server implemented in a web services environment (e.g., Amazon Web Services), with an interface to the Assistant to exchange information with the patient, and logic to implement.

The data layer 306 may include one or more data store systems with a database or file system wherein data is stored. As previously described, the data may be patient information, medical data, caregiver data, device data, iterations thereof, or some combination thereof. The one or more data systems may be a contemporary remote service data store system, a web services storage system, or some combination thereof.

Figure 4:
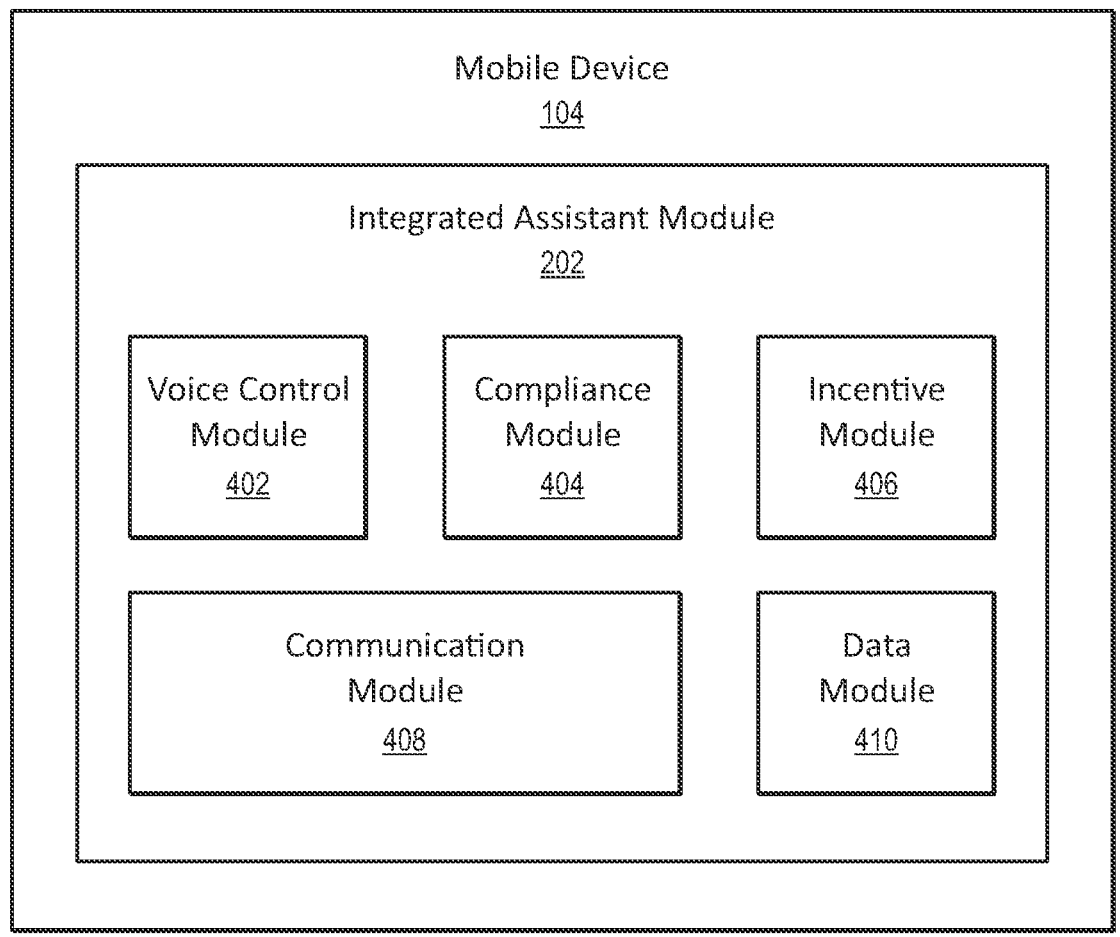
FIG. 4 is a diagram of a mobile device in accordance with exemplary embodiments described herein.

FIG. 4 is a block diagram illustrating components of one example of a mobile device 104. The mobile device 104 may be an example of the mobile device 104 described with reference to FIGS. 1 and 2. In this example, the mobile device 104 has an integrated assistant module 202. The integrated assistant module 202 may include a voice control module 402, compliance module 404, incentive module 406, communication module 408, and data module 410.

The voice control module 402 may act as a virtual assistant. For example, the voice control module 402 may enable a patient to use voice recognition and voice activation technology. In some embodiments, the voice control module 402 may communicate with commercially available voice control modules such as, for example, Google Assistant®, Siri®, or Alexa®, which are available on several commercially available smart devices. Virtual assistants may perform actions including phone actions, searching the net for requested information, scheduling events and reminders, handling device settings, navigating areas, finding entertainment, and, in some embodiments, may engage with third party devices and apps. Virtual assistants may also support follow-up questions and language translations.

In some embodiments, the voice control module 402 integrates and communicates with the virtual assistant on a mobile device 104 so that a patient wearing a cardiac device may use virtual assistant to check on the status of the cardiac device. The patient may be able to check their health status as well including heart health and movement. In further embodiments, the voice control module 402 may integrate and communicate with other virtual assistants such as an Amazon Echo® or a Nest® device from Google®.

In some embodiments, the virtual control module 402 may, through the virtual assistant, identify the voice of patient and respond to commands related to the cardiac device when the patient's voice identification is confirmed. In further embodiments, the virtual control module 402 may grant cardiac device permissions or other settings to the patient, service technician, the patient's physician, other health service provider, or some combination thereof. Each person with access to the cardiac device may have their own profile granting explicit permissions of control and access to the cardiac device. For example, the virtual control module 402 may respond to a patient's request for cardiac device information and convey the information via audio output devices proximate the mobile device 104. In some embodiments, the information may be displayed as text, picture, or video information on the screen of the mobile device 104.

In some embodiments, the voice control module 402 may respond to non-patient voice requests when a predetermined event occurs. For example, if the cardiac device is a WCD and is about to deliver a shock to the patient, the voice control module 104 listen to and respond to bystanders' questions. The responses maybe limited to assisting the patient during the emergency event. For example, if a bystander asks, "What can I do to help?" or "What is happening?" the voice control module 402 may detect the voice commands and transmit the commands to the communication module 408 which may respond with voice commands such as "Patient is experiencing a cardiac event, dispensing shock, stand back and give the patient space."

The compliance module 404 may monitor compliance activities by the patient. In some embodiments, the compliance module 404 may monitor compliance activities with rules for alerting the patient, medical personnel, other stakeholders, caregivers, or some combination thereof. The rules may be directed to the patient's compliance with goals or other activities set by appropriate personnel. In some embodiments, the personnel may be able to remotely alter the compliance goals while the patient is using the cardiac device. In some embodiments, the cardiac device may collect compliance data on a periodic basis even if no alerts were generated. For example, compliance module 404 may retrieve patient compliance data from the cardiac device on a predetermined schedule. The predetermined schedule may be an hourly basis or may be longer or shorter. In some embodiments, the predetermined basis may change depending on the memory and power resources of the cardiac device.

The compliance module 404 may monitor compliance of multiple items. In one embodiment, the compliance module 404 may monitor cardiac device wearability. The cardiac device wearability may monitor when the patient is and is not wearing the cardiac device. In some embodiments, the compliance module 404 may have a wearability threshold. Once the threshold is surpassed, the compliance module 404 may ping the communication module 408 which may send an alert to the patient and the appropriate medical personnel. The medical personnel may set the wearability threshold. In some embodiments, the medical personnel may have the authority to set and change the threshold. For example, the threshold may default to a 48-hour period of non-wearability. However, medical personnel may remotely alter the threshold to a shorter time period (e.g., to a 24-hour period) so that alerts will be triggered if the patient continues to be non-compliant with this behavior.

Other examples of compliance thresholds include rules related to activity duration, maximum inactive period while awake, sleep duration, step counts, average wear-time per week, maximum non-wear time in a day, maximum time between battery swaps, maximum time to respond to messages sent to the patient via integrated assistant module 202, and the like. In some embodiments, new rules and thresholds may be remotely created and added to the compliance module 404. Likewise, existing compliance rules and thresholds may be altered, deleted, or both.

In some embodiments, a service provider can program the initial thresholds for compliance activities which are provided to the service provider by the doctor during a fitting and training process for the patient. The thresholds may be altered later by the medical personnel, for example, in response to compliance data, patient feedback, frequency of alerts, or changes in the patient's health and wellness. In some embodiments, some thresholds may also be maintained by other stakeholders, such as a physical therapist, wellness counselor, mindfulness coach, and the like. In some embodiments, each threshold may be permission-based such that only qualified persons can modify rules and thresholds.

The incentive module 406 may provide real and virtual incentives to patients for achieving the compliance goals as monitored by the compliance module 504. In some embodiments, the incentives may be real incentives such as gift cards when compliance thresholds are met. In other embodiments, the incentives may be virtual incentives such as badges, new avatar features or accessories, and the like. Real and virtual incentives may increase engagement with patients to encourage compliance with cardiac device requirements and to perform activities intended to promote wellness.

In some embodiments, the incentive module 406 may additionally or alternatively provide real and virtual incentives to a patient when various activities are performed. The activities may be related to the proper cardiac device, wellness activities, and engagement activities, and the like.

In some embodiments, the incentive module 406 may receive information regarding the set up and operation of the cardiac device. For example, in the case of a WCD, the patient may receive operating instructions on the use and maintenance of the WCD. The instructions may include training, wear compliance, battery life and charging, washing and cleanliness, return instructions in rental scenarios, and the like or some combination thereof. The compliance module 404 may determine when the set-up instructions have been read and, in some instances, completed. The incentive module may then provide one or more rewards upon completion.

In some embodiments, the incentive module 406 may provide incentives when wellness thresholds are satisfied. For example, the cardiac device may interact with the patient to set and monitor activity goals intended to improve the patient's wellness, both physical and mental/emotional. In some embodiments, the wellness thresholds are implemented as disclosed in U.S. Prov. App. No. 63/069,627, previously mentioned. In other embodiments, data related to the compliance activities are recorded by the cardiac device, or the incentive module 406, which may be communicated to the companion module (e.g., companion module 204, FIG. 2) and communicated to the various entities as necessary. Activity goals may include total steps, distance, exercise, heart rate during exercise, calories burned, mindfulness, sleep, stretching, active minutes, and the like. In some embodiments, the incentive module 406 may additionally distribute surveys or questionnaires to poll the patient.

The incentive module 406 may award tangible rewards, virtual rewards, or some combination thereof. The tangible rewards may send the patient an "e-voucher" or gift cards from a retailer (e.g., a healthy food or beverage retailer, a virtual exercise class, or a virtual mindfulness session, airline miles, music, discounts for athletic clothing, etc.). In some embodiments, the incentive module 406 automatically sends the incentive to the patient for immediate realization of the reward enhancing the patient's experience and linkage of the award to the goal achievement. In some embodiments, the incentive module 406 may allow the patient can choose among various e-vouchers or gift cards. The incentive module 406 may have awards to increase patient engagement and compliance, while promoting healthy food choices and exercise.

The incentive module 406 may also issue virtual awards. The virtual awards may include badges, display of celebratory images or GIFs, new themes for the app, and the like. In some embodiments, the virtual awards may include additional clothing or accessories for the patient's avatar, changing the appearance of the avatar with clothing, facial expressions, accessories, and the like.

In some embodiments, the incentive module 406 may issue awards to motivate patients. For example, when the patient maintains a sedentary or unhealthy condition, the incentive module 406 may trigger a prompt or action that could appropriately promote wellness. For example, the incentive module 406 may receive information that the patient has been seated for an extended period of time (e.g., an hour). In response, the incentive module 406 may play a song (e.g., "The Hokey Pokey") and announce an award (e.g., "Do the Hokey Pokey and get a free smoothie from Jamba Juice!! !"). If the system detects the patient got up and moved, the incentive module 406 may issue the award. In another example, the incentive module 406 may receive information that the patient is experiencing a high stress level (e.g., patient is not active but has an elevated heart rate). The incentive module 406 may prompt a mindfulness activity and appropriate incentive award if the patient completes the mindfulness activity.

The communication module 408 may provide notifications to the patient, doctor, or other stakeholder. The notifications may be specific to the participant. For example, the notifications for the medical personnel may be different than notifications for the cardiac device provider. The communication module 408 may cause one or more notifications or alerts to issue. For example, the communication module 408 may cause a safety alarm, a physiological alarm, a system alarm, or any other alarm related to the cardiac device to issue. The notification may have multiple components. For example, the notification may have a multi-visual component, an audible component, and a haptic component. The multi-visual component may include a light(s), a visual display including a GUI, or some combination thereof. The visual component may use the light(s) to garnish the attention of the user and may display a written message or coded message on a screen. The audible alarm may be an alert or may be a spoken alarm relaying a message concerning the cardiac device or patient condition The data module 410 may track all the patient data include heart data, device data, compliance data and the like. In some embodiments, the data module 410 may be a learning module. For example, the data module 410 may be trained using inputs from the patient about likes and dislikes, hobbies, interests, mobility level over time. Once the information is collected, the data module 410 may use the information in formulating a response when the patient uses the virtual assistant. For example, in some responses, the communication module 408 may suggest topics and offer information of interest to the individual within one or more categories that are responsive to the input received from the patient based on the learning algorithm in the data module 410. For example, the data module 410 may have suggestions based at least in part on the individual's cardiac condition, other health concerns, habits, nutritional factors, allergies, likes, dislikes, other preferences, or some combination thereof.

In some embodiments, the data module 410 may obtain the patient's visual expressions, such as pain, laughter, smile, sadness, etc. The data module 410 may analyze the information better respond to patient's input received via the virtual assistant. Data module 410 may then supplement integrated assistant module 202 advice and suggestions with this additional information.

Figure 5:
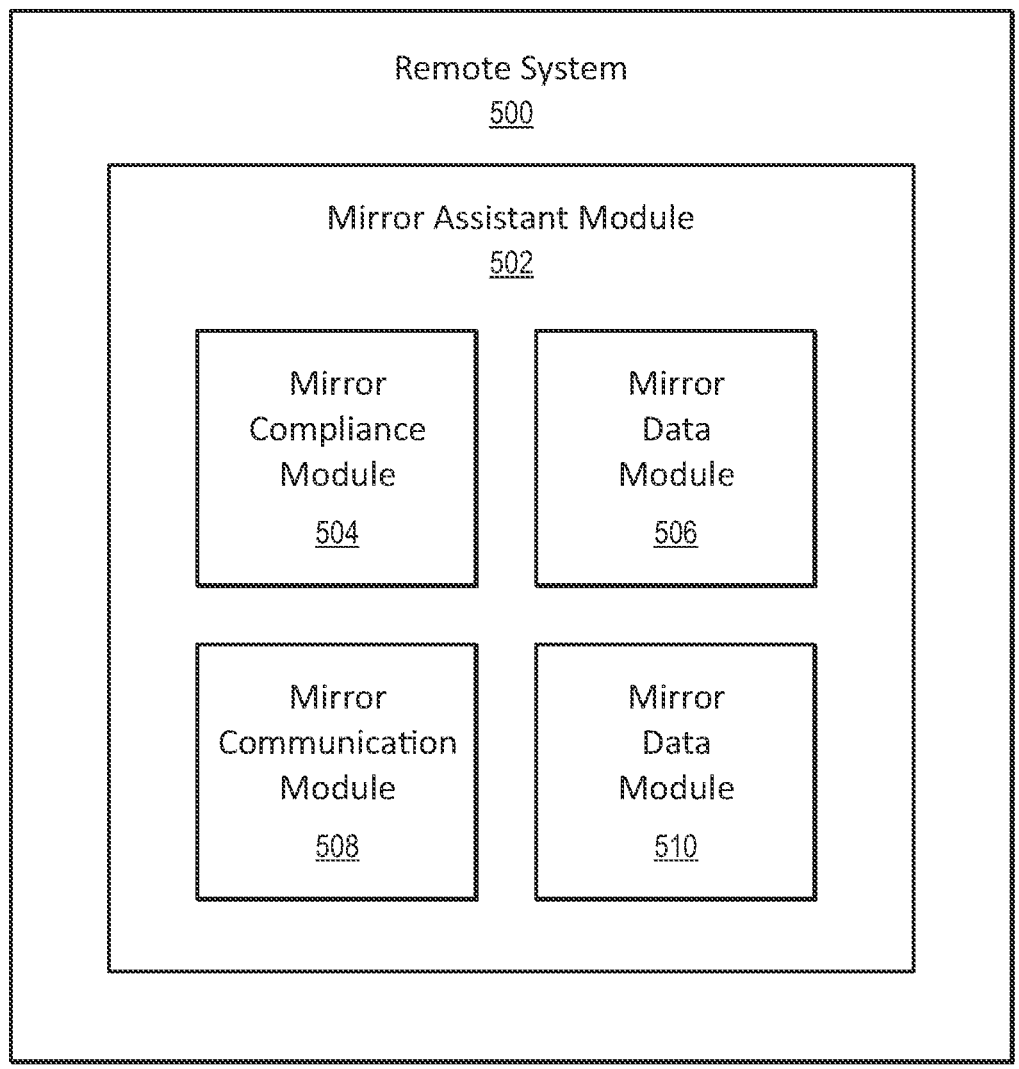
FIG. 5 is a diagram of a remote system in accordance with exemplary embodiments described herein.

FIG. 5 is a block diagram illustrating components of one example of a remote system 500. The remote system 500 may be an example of the medical system 106, customer service cloud 108, CRM system 110, and care station 112 described with reference to FIGS. 1 and 2. The remote system 500 may also be an example of a device used by appropriate personnel to access of the systems (e.g., medical system 106, customer service cloud 108, CRM system 110, and care station 112). For example, a doctor may use their mobile device or a laptop to access the medical system 106. In this example, the remote system 500 has a mirror assistant module 502. The mirror assistant module 502 may include a mirror module 502, mirror compliance module 504, mirror incentive module 506, communication module 510, and a mirror data module 512.

The mirror assistant module 502 may provide one or more advantages. In some scenarios, the mirror assistant module 502 may allow a doctor, customer service representative, or CRM personnel to check the status of a patient, cardiac device, or both. The mirror assistant module 502 may enable participants to view the patient's compliance information, health and device data, and incentives. The participants may also use the communication module 508 to directly communicate to the patient via the assistant module 402.

In embodiments, system personnel may have mirror applications on their workstations, mobile devices, laptops, tablets, or some combination thereof. For example, the mirror module 504 may receive information from the integrated assistant module 202 and "mirror" the information from the integrated assistant module 202 to the appropriate sub-modules in the mirror assistant module 504. This enables the personnel to see what information the patient is viewing and respond, if needed.

In some embodiments, the mirror module 504 is programmed with various roles and permissions. For example, as discussed previously, each personnel has varying levels of access to varying types of information. For example, the medical personnel does not need to know about battery life of the cardiac device and the device manufacturer doesn't need personal information to debug situations remotely. In further examples, the medical personnel may be granted access to the personal health information of the patient, while the CRM personnel does not.

In some embodiments, the communication module 510 may get notifications from the mirror module 504 alerting the non-patient personnel of an event or other occurrence received from the cardiac device or detected by the integrated assistant module 204. In some embodiments, the personnel may be prompted to call emergency personnel, check on the patient, call the patient to troubleshoot system issues, and the like.

In some embodiments, the participants may have access to compliance module 404 through the mirror compliance module 506 and the incentive module 406 through the mirror incentive module 508. In some embodiments, the participants may change compliance goals, incentive rewards, or both. For example, medical personnel may set an initial wear-time compliance goal and then adjust the goals in response to the patient's habits and compliance. If the patient is meeting or exceeding a wear threshold and being rewarded, the participants may alter the wear threshold, the incentives for meeting the threshold, or set entirely new goals.

FIG. 6 illustrates an exemplary cardiac device system 600 with a patient 602 wearing an example of a WCD system 604 according to embodiments described herein. In some embodiments, the WCD system 604 may be an example of the cardiac device 102 described with reference to FIGS. 1 and 2. In some embodiments, the WCD 602 may include one or more communication devices 606, a support structure 610, and an external defibrillator 608 connected to two or more defibrillation electrodes 614, 616, among other components. In still further embodiments, the cardiac device 602 may be another type of cardiac device which may contain one or more combinations of components described herein.

The support structure 610 may be worn by the patient 602. The patient 602 may be ambulatory, meaning the patient 602 can walk around and is not necessarily bed-ridden while wearing the wearable portion of the cardiac device 604. While the patient 602 may be considered a "user" of the cardiac device 604, this is not a requirement. For instance, a user of the cardiac device 604 may also be a clinician such as a doctor, nurse, emergency medical technician (EMT), or other similarly tasked individual or group of individuals. In some cases, a user may even be a bystander. The particular context of these and other related terms within this description should be interpreted accordingly.

In some embodiments, the support structure 610 may include a vest, shirt, series of straps, or other system enabling the patient 602 to carry at least a portion of the cardiac device 604 on the patient's body. In some embodiments, the support structure 610 may comprise a single component. For example, the support structure 610 may comprise a vest or shirt that properly locates the cardiac device 604 on a torso 612 of the patient 602. The single component of the support structure 610 may additionally carry or couple to all of the various components of the cardiac device 604.

In other embodiments, the support structure 610 may comprise multiple components. For example, the support structure 610 may include a first component resting on a patient's shoulders. The first component may properly locate a series of defibrillation electrodes 614, 616 on the torso 612 of the patient 602. A second component may rest more towards a patient's hips, whereby the second component may be positioned such that the patient's hips support the heavier components of the cardiac device 604. In some embodiments, the heavier components of the cardiac device 604 may be carried via a shoulder strap or may be kept close to the patient 602 such as in a cart, bag, stroller, wheelchair, or other vehicle.

In some embodiments, the support structure 610 can be worn by being attached to the body of the patient 602 by adhesive material, for example as shown and described in U.S. Pat. No. 8,024,037, incorporated herein in its entirety by reference. In some embodiments, the support structure 610 can be implemented as described in U.S. Patent Publication No. 20170056682, incorporated herein in its entirety by reference. In still further embodiments, additional components of the cardiac device 604 may incorporated in the housing of the support structure 610 instead of being attached externally to the support structure 610. One example is described in U.S. Patent Publication No. 20170056682, incorporated herein in its entirety by reference.

The external defibrillator 608 may be coupled to the support structure 610 or may be carried remotely from the patient 602. The external defibrillator 608 may be triggered to deliver an electric shock to the patient 602 when patient 602 wears the cardiac device 604. For example, if certain thresholds are exceeded or met, the external defibrillator 608 may engage and deliver a shock to the patient 602.

The defibrillation electrodes 614, 616 can be configured to be worn by patient 602 in a number of ways. For instance, the defibrillator 608 and the defibrillation electrodes 614, 616 can be coupled to the support structure 610 directly or indirectly. For example, the support structure 610 can be configured to be worn by the patient 602 to maintain at least one of the electrodes 614, 616 on the body of the patient 602, while the patient 602 is moving around, etc. The electrodes 614, 616 can be thus maintained on the torso 612 by being attached to the skin of patient 602, simply pressed against the skin directly or through garments, etc. In some embodiments, the electrodes 614, 616 are not necessarily pressed against the skin but becomes biased that way upon sensing a condition that could merit intervention by the WCD system 604. In addition, many of the components of defibrillator 108 can be considered coupled to support structure 610 directly, or indirectly via at least one of defibrillation electrodes 614, 616.

The WCD system 604 may defibrillate the patient 602 by delivering an electrical charge, pulse, or shock 611 to the patient 602 through a series of electrodes 614, 616 positioned on the torso 612. For example, when defibrillation electrodes 614, 616 are in good electrical contact with the torso 612 of patient 1502, the defibrillator 608 can administer, via electrodes 614, 616, a brief, strong electric pulse 611 through the body. The pulse 611 is also known as shock, defibrillation shock, therapy, electrotherapy, therapy shock, etc. The pulse 611 is intended to go through and restart the heart 622, in an effort to save the life of patient 602. The pulse 611 can further include one or more pacing pulses of lesser magnitude to pace heart 622 if needed. The electrodes 614, 616 may be electrically coupled to the external defibrillator 608 via a series of electrode leads 618. The defibrillator 608 may administer an electric shock 611 to the body of the patient 602 when the defibrillation electrodes 614, 616 are in good electrical contact with the torso 612 of patient 602. In some embodiments, devices (not shown) proximate the electrodes 614, 616 may emit a conductive fluid to encourage electrical contact between the patient 602 and the electrodes 614, 616.

In some embodiments, the cardiac device 604 may also include either an external or internal monitoring device or some combination thereof. FIG. 6 displays an external monitoring device 624 which may also be known as an outside monitoring device. The monitoring device 624 may monitor at least one local parameter. Local parameters may include a physical state of the patient 602 such as ECG, movement, heartrate, pulse, temperature, and the like. Local parameters may also include a parameter of the cardiac device 604, environmental parameters, or the like. For example, in some embodiments, the monitoring device 624 may include sensors to gather patient movement, ambient lighting, and the like. The monitoring device 624 may be physically coupled to the support structure 610 or may be proximate the support structure 610. In either location, the monitoring device 624 is communicatively coupled with other components of the cardiac device 604.

For some of these parameters, the device 624 may include one or more sensors or transducers. Each one of such sensors can be configured to sense a parameter of the patient 602, and to render an input responsive to the sensed parameter. In some embodiments, the input is quantitative, such as values of a sensed parameter; in other embodiments, the input is qualitative, such as informing whether or not a threshold is crossed. In some instances, these inputs about the patient 602 are also referred to herein as patient physiological inputs and patient inputs. In some embodiments, a sensor can be construed more broadly as encompassing many individual sensors.

In some embodiments, a communication device 606 may enable the patient 602 to interact with, and garnish data from, the cardiac device 604. The communication device 606 may enable a patient or third party to view patient data, dismiss a shock if the patient is still conscious, turn off an alarm, and otherwise engage with the WCD system 604. In some instances, the communication device 606 may transfer or transmit information include patient data to a third-party data server such as a cloud server or a blockchain server. In some embodiments, the communication device 606 may be a separable part of an external defibrillator 608. For example, the communication device 606 may be a separate device coupled to the external defibrillator 608. In some embodiments, the communication device 606 may be wired or wirelessly linked to the external defibrillator 608 and may be removable from the defibrillator 608. In other embodiments, the communication device 606 may form an inseparable assembly and share internal components with the external defibrillator 608. In some embodiments, the cardiac device 604 may include more than one communication devices 606. For example, the defibrillator 608 may include components able to communicate to the patient and the WCD system 604 may include a separate communication device 606 remote from the defibrillator 608.

In some embodiments, the communication device 606 may be communicatively coupled to an alert button 628. The alert button 628 may be removably coupled to the support structure 610. The patient 602 may couple the alert button 628 to the support structure 610 or may couple the alert button 628 to an article of clothing. The alert button 628 may have a wired connection or be wirelessly connected to the communication device 606. In some embodiments, the alert button 628 may include a visual output, an audio output, and a user input. The visual output may include a light, such as an LED, a small screen, or some combination thereof.

Likewise, the audio output may include one or more speakers. The output of the audio output may be loud enough to be heard over nominal background noise. In some embodiments, the audio output might have an adjustable volume range. In some embodiments, the alert button 628 may include a microphone. In still further embodiments, the alert button 628 may also include a haptic response.

In some embodiments, the defibrillator 608 may connect with one or more external devices 626. For example, as shown in FIG. 6, the defibrillator 608 may connect to various external devices 626 such as the cloud, a remote desktop, a laptop, a mobile device (e.g., mobile device 104), or other external device using a network such as the Internet, local area networks, wide area networks, virtual private networks (VPN), other communication networks or channels, or any combination thereof.

In embodiments, one or more of the components of the exemplary cardiac device 604 may be customized for the patient 602. Customization may include a number of aspects including, but not limited to, fitting the support structure 610 to the torso 612 of patient 602; baseline physiological parameters of patient 602 can be measured, such as the heart rate of patient 602 while resting, while walking, motion detector outputs while walking, etc. The measured values of such baseline physiological parameters can be used to customize the cardiac device 604 to make its analysis more accurate since patients' bodies differ from one another. Of course, such parameter values can be stored in a memory of the cardiac device 604 and the like. Moreover, a programming interface can be made according to embodiments, which receives such measured values of baseline physiological parameters. Such a programming interface may input automatically in the cardiac device 604 these, along with other data.

Figure 7:
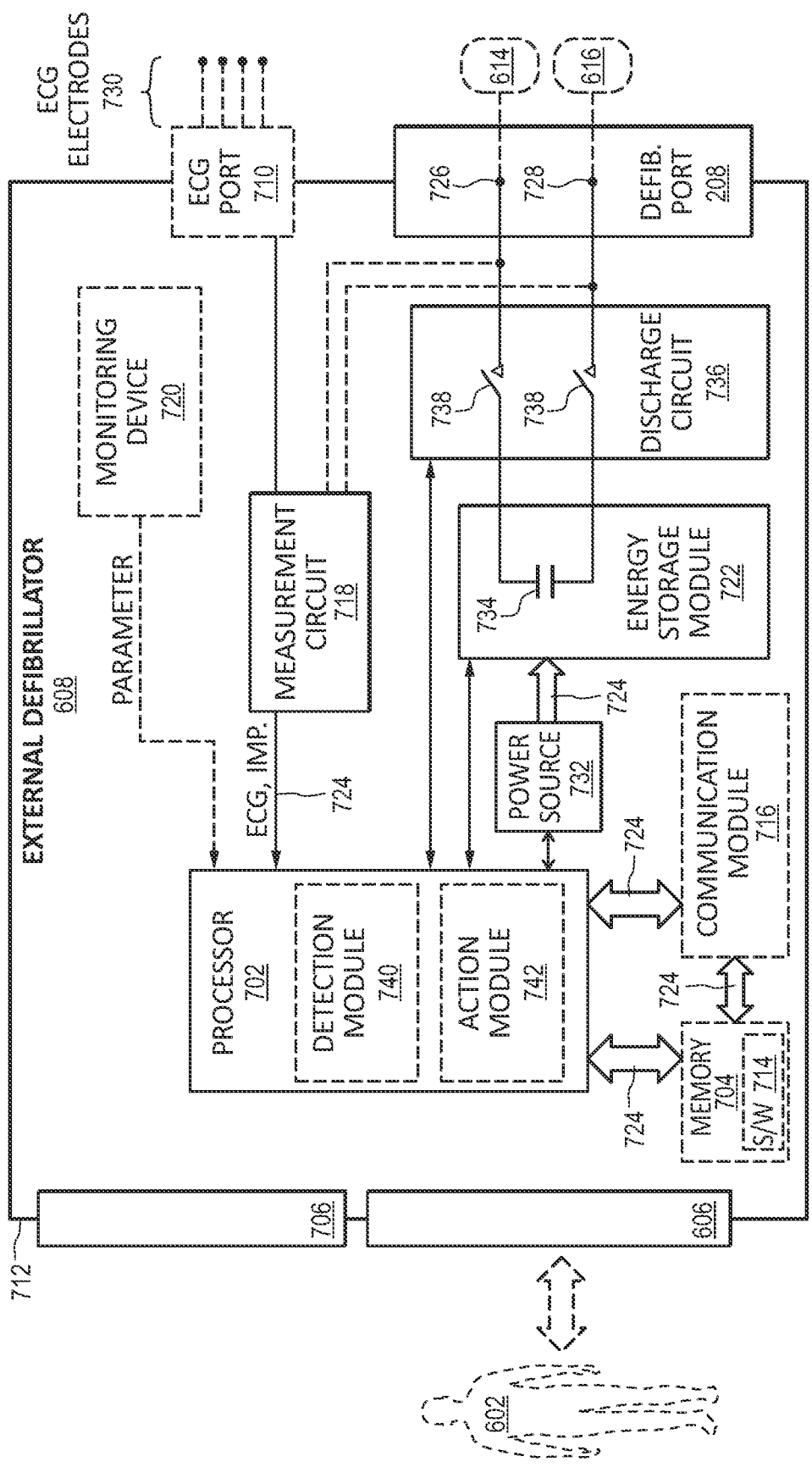
FIG. 7 is a block diagram of an example wearable cardiac monitoring device in accordance with exemplary embodiments described herein.

FIG. 7 is a diagram displaying various components of an example external defibrillator 608. The external defibrillator 608 may be an example of the defibrillator 608 described with reference to FIG. 6. The components shown in FIG. 7 may be contained within a single unit or may be separated amongst two or more units in communication with each other. The defibrillator 608 may include a communication device 706, processor 702, memory 704, defibrillation port 708, and ECG port 710, among other components. In some embodiments, the components are contained within a housing 712 or casing. The housing 712 may comprise a hard shell around the components or may comprise a softer shell for increased patient comfort.

The communication device 706, processor 702, memory 704 (including software/firmware code (SW) 714), defibrillation port 708, ECG port 710, communication module 716, measurement circuit 718, monitoring device 720, and energy storage module 722 may communicate, directly or indirectly, with one another via one or more buses 724. The one or more buses 724 may allow data communication between the elements and/or modules of the defibrillator 608.

The memory 704 may include random access memory (RAM), read only memory (ROM), flash RAM, and/or other types. The memory 704 may store computer-readable, computer-executable software/firmware code 714 including instructions that, when executed, cause the processor 702 to perform various functions (e.g., determine shock criteria, determine heart rate, issue shock command, issue alerts, etc.). In some embodiments, the processor 702 may include an intelligent hardware device, e.g., a central processing unit (CPU), a microcontroller, an application-specific integrated circuit (ASIC), etc.

In some embodiments, the memory 704 can contain, among other things, the Basic Input-Output system (BIOS) which may control basic hardware and/or software operations such interactions and workings of the various components of the defibrillator 608, and in some embodiments, components external to the defibrillator 608. For example, the memory 704 may contain various modules to implement the workings of the defibrillator 608 and other aspects of the present disclosure.

In some embodiments, the defibrillator 608 may include a user interface 706. The user interface 706 may be in addition to or part of the communication device 706. The user interface 706 may display an ECG of the patient, a status of the defibrillator 608, a status of a charge (e.g., a battery charge or an energy storage module), and the like.

In some embodiments, the user interface 706 may include output devices, which may include visual, audible, or tactile, for communicating to a user by outputting images, sounds or vibrations. Images, sounds, vibrations, and an alert or notification that can be perceived by a person is also called human-perceptible indications (HPIs). Output devices, or HPIs, may include a light(s), a screen to display what is sensed, detected and/or measured, speakers, and the like. In some embodiments, the screen may provide visual feedback to a third party for their resuscitation attempts and treatment plans. In some embodiments, the speaker may be configured to issue voice prompts, beeps, loud alarm sounds and/or words to warn bystanders, etc.

In some embodiments, the user interface 706 may further include input devices for receiving inputs from users. Such input devices may include various controls, such as push-buttons, keyboards, touchscreens, one or more microphones, and so on. An input device can be a cancel switch, which is sometimes called an "I am alive" switch or "live man" switch. In some embodiments, actuating the cancel switch can prevent the impending delivery of a shock.

In some embodiments, the defibrillator 608 may include a defibrillation port 708. The defibrillation port 708 may comprise a socket, opening, or electrical connection in the housing 712. In some instances, the defibrillation port 708 may include two or more nodes 726, 728. The two or more nodes 726, 728 may accept two or more defibrillation electrodes (e.g., defibrillation electrodes 614, 616, FIG. 6). The nodes 726, 728 may provide an electrical connection between the defibrillation electrodes 614, 616 and the defibrillator 608. The defibrillation electrodes 614, 616 may plug into the two or more nodes 726, 728 via one or more leads (e.g., leads 618), or, in some instances, the defibrillation electrodes 614, 616 may be hardwired to the nodes 726, 728. Once an electrical connection is established between the defibrillation port 708 and the electrodes 614, 616, the defibrillator 608 may be able to deliver an electric shock to the patient 602.

In some embodiments, the defibrillator 608 may include an ECG port 710 in the housing 712. The ECG port 710 may accept one or more ECG electrodes 730 or ECG leads. In some instances, the ECG electrodes 730 sense a patient's ECG signal. For example, the ECG electrodes 730 may record electrical activity generated by heart muscle depolarization, timing, or both. The ECG electrodes 730 may utilize 4-leads to 12-leads or multichannel ECG, or the like. The ECG electrodes 730 may connect with the patient's skin.

In some embodiments, the defibrillator 608 may include a measurement circuit 718. The measurement circuit 718 may be in communication with the ECG port 710. For example, the measurement circuit 718 may receive physiological signals from ECG port 710. The measurement circuit 718 may additionally or alternatively receive physiological signals via the defibrillation port 708 when defibrillation electrodes 614, 616 are attached to the patient 662. The measurement circuit 718 may determine a patient's ECG signal from a difference in voltage between the defibrillation electrodes 614, 616.

In some embodiments, the measurement circuit 718 may monitor the electrical connection between the defibrillation electrodes 614, 616 and the skin of the patient 602. For example, the measurement circuit 718 can detect impedance between electrodes 614, 616. The impedance may indicate the effective resistance of an electric circuit. An impedance calculation may determine when the electrodes 614, 616 have a good electrical connection with the patient's body.

If, in some embodiments, the defibrillator 608 lacks a sensor port, the measurement circuit 718 may obtain physiological signals through nodes 726, 728 when defibrillation electrodes 614, 616 are attached to the patient. The input may reflect an ECG measurement. The patient parameter can be an ECG, which can be sensed as a voltage difference between electrodes 614, 616. In addition, the patient parameter may be an impedance, which may be sensed between electrodes 614, 616 and/or between the connections of sensor port considered pairwise. In some embodiments, the impedance may be used to determine when electrodes 614, 616 and/or sensing electrodes are not making good electrical contact with the patient's body.

In some embodiments, the defibrillator 608 may include an internal monitoring device 720 within the housing 712. The monitoring device 720 may monitor at least one local parameter. Local parameters may include physical state of the patient such as ECG, movement, heartrate, pulse, temperature, and the like. Local parameters may also include a parameter of the cardiac device (e.g., cardiac device 604, FIG. 6), defibrillator 608, environmental parameters, or the like.

In some embodiments, the WCD system 604 may include an internal monitoring device 720 and an external monitoring device (e.g., external monitoring device 624). If both monitoring devices 624, 720 are present, the monitoring devices 624, 720 may work together to parse out specific parameters depending on position, location, and other factors. For example, the external monitoring device 624 may monitor environmental parameters while the internal monitoring device 720 may monitor patient and system parameters.

Patient parameters may include patient physiological parameters. Patient physiological parameters may the WCD system in detecting when the patient is in need of a shock or other intervention or assistance. Patient physiological parameters may also include the patient's medical history, event history, and the like. Examples of such parameters may include the patient's ECG, blood oxygen level, blood flow, blood pressure, blood perfusion, pulsatile change in light transmission or reflection properties of perfused tissue, heart sounds, heart wall motion, breathing sounds and pulse.

The internal and external monitoring devices 720, 624 may include one or more sensors configured to acquire patient physiological signals. For example, either one or both monitoring devices 720, 624 may include one or more electrodes to detect ECG data, a perfusion sensor, a pulse oximeter, a device for detecting blood flow (e.g., a Doppler device), a sensor for detecting blood pressure (e.g., a cuff), an optical sensor, illumination detectors and sensors perhaps working together with light sources for detecting color change in tissue, a motion sensor, a device that can detect heart wall movement, a sound sensor, a device with a microphone, an SpO2 sensor, and so on.

In some embodiments, the local parameter is a trend that can be detected in a monitored physiological parameter of patient. A trend can be detected by comparing values of parameters at different times over short and long terms. Parameters whose detected trends can particularly help a cardiac rehabilitation program may include: a) cardiac function (e.g. ejection fraction, stroke volume, cardiac output, etc.); b) heart rate variability at rest or during exercise; c) heart rate profile during exercise and measurement of activity vigor, such as from the profile of an accelerometer signal and informed from adaptive rate pacemaker technology; d) heart rate trending; e) perfusion, such as from SpO2, CO2, or other parameters such as those mentioned above, f) respiratory function, respiratory rate, etc.; g) motion, level of activity; and so on. Once a trend is detected, it can be stored and/or reported via a communication link, along perhaps with a warning if warranted. The report may aid a physician in monitoring the progress of patient.

In some embodiments, the monitoring devices 720, 624 may include sensors that monitor external conditions. For example, the monitoring devices may monitor environmental parameters. Environmental parameters may include ambient temperature, pressure, humidity, and the like.

In some embodiments, the defibrillator 608 may include a power source 732. The power source 732 may comprise a battery or battery pack, which may be rechargeable. In some instances, the power source 732 may comprise a series of different batteries to ensure the defibrillator 608 has power. For example, the power source 732 may include a series of rechargeable batteries as a prime power source and a series of non-rechargeable batteries as a secondary source. If the patient 602 is proximate an AC power source, such as when sitting down, sleeping, or the like, the power source 732 may include an AC override wherein the power source 732 draws power from the AC source.

In some embodiments, the defibrillator 608 may include an energy storage module 722. The energy storage module 722 may store electrical energy in preparation or anticipation of providing a sudden discharge of electrical energy to the patient. In some embodiments, the energy storage module 722 may have its own power source and/or battery pack. In other embodiments, the energy storage module 722 may pull power from the power source 732. In still further embodiments, the energy storage module 722 may include one or more capacitors 734. The one or more capacitors 734 may store an electrical charge, which may be administered to the patient. The processor 702 may be communicatively coupled to the energy storage module 722 to trigger the amount and timing of electrical energy to provide to the defibrillation port 708 and, subsequently, the patient 602.

In some embodiments, the defibrillator 608 may include a discharge circuit 736. The discharge circuit 736 may control the energy stored in the energy storage module 722. For example, the discharge circuit 736 may either electrical couple or decouple the energy storage module 722 to the defibrillation port 708. The discharge circuit 736 may be communicatively coupled to the processor 702 to control when the energy storage module 722 and the defibrillation port 708 should or should not be coupled to either administer or prevent a charge from emitting from the defibrillator 608. In some embodiments, the discharge circuit 736 may include one or more switches 738. In further embodiments, the one or more switches 738 may include an H-bridge.

In some embodiments, the defibrillator 608 may include a communication module 716. The communication module 716 may establish one or more communication links with either local hardware and/or software to the cardiac device 604 and defibrillator 608 or to remote hardwire separate from the cardiac device 604. In some embodiments, the communication module 716 may include one or more antennas, processors, and the like. The communication module 716 may communicate wirelessly via radio frequency, electromagnetics, local area networks (LAN), wide area networks (WAN), virtual private networks (VPN), RFID, Bluetooth, cellular networks, and the like. The communication module 716 may facilitate communication of data and commands such as patient data, episode information, therapy attempted, CPR performance, system data, environmental data, and so on. In some embodiments, the communication module 716 may include a display screen to display messages to the patient. In some embodiments, the display screen may be a touch screen, backlit screen, passive, reflective LCD screen or the like.

In further embodiments, the communication module 716 may include one or more LEDs which may also be used to convey information to the patient. In some embodiments, the LED brightness may be modulated, the LEDs may be color changing, and the like. In some embodiments, if multiple LEDs are present, each LED may represent various bits of information. For example, one LED may represent heartrate information and enable the patient to quickly determine their heart is operating normally. Another LED may represent the heartrate signal to ensure the patient the heartrate readings are being properly transmitted. Another LED may also represent system status and allow the patient to easily ascertain that the system is fully functioning.

In some embodiments, the processor 702 may execute one or more modules. For example, the processor 702 may execute a detection module 740 and/or an action module 742. The detection module 740 may be a logic device or algorithm to determine if any or a variety of thresholds are exceeded which may require action of the defibrillator 608. For example, the detection module 740 may receive and interpret all of the signals from the ECG port 710, the defibrillation port 708, the monitoring device 720, an external monitoring device, and the like. The detection module 740 may process the information to ensure the patient is still conscious and healthy. If any parameter indicates the patient 602 may be experiencing distress or indicating a cardiac episode, the detection module 740 may activate the action module 742.

The action module 742 may receive data from the detection module 740 and perform a series of actions. For example, an episode may merely be a loss of battery power at the power source 732 or the energy storage module 722, or one or more electrodes (e.g., ECG electrodes, defibrillation electrodes) may have lost connection. In such instances, the action module 742 may trigger an alert to the patient or to an outside source of the present situation. This may include activating an alert module. If an episode is a health risk, such as a cardiac event, the action module 742 may begin a series of steps. This may include issuing a warning to the patient, issuing a warning to a third party, priming the energy storage module 722 for defibrillation, releasing one or more conductive fluids proximate defibrillation electrodes 614, 616, and the like.

Figure 8:
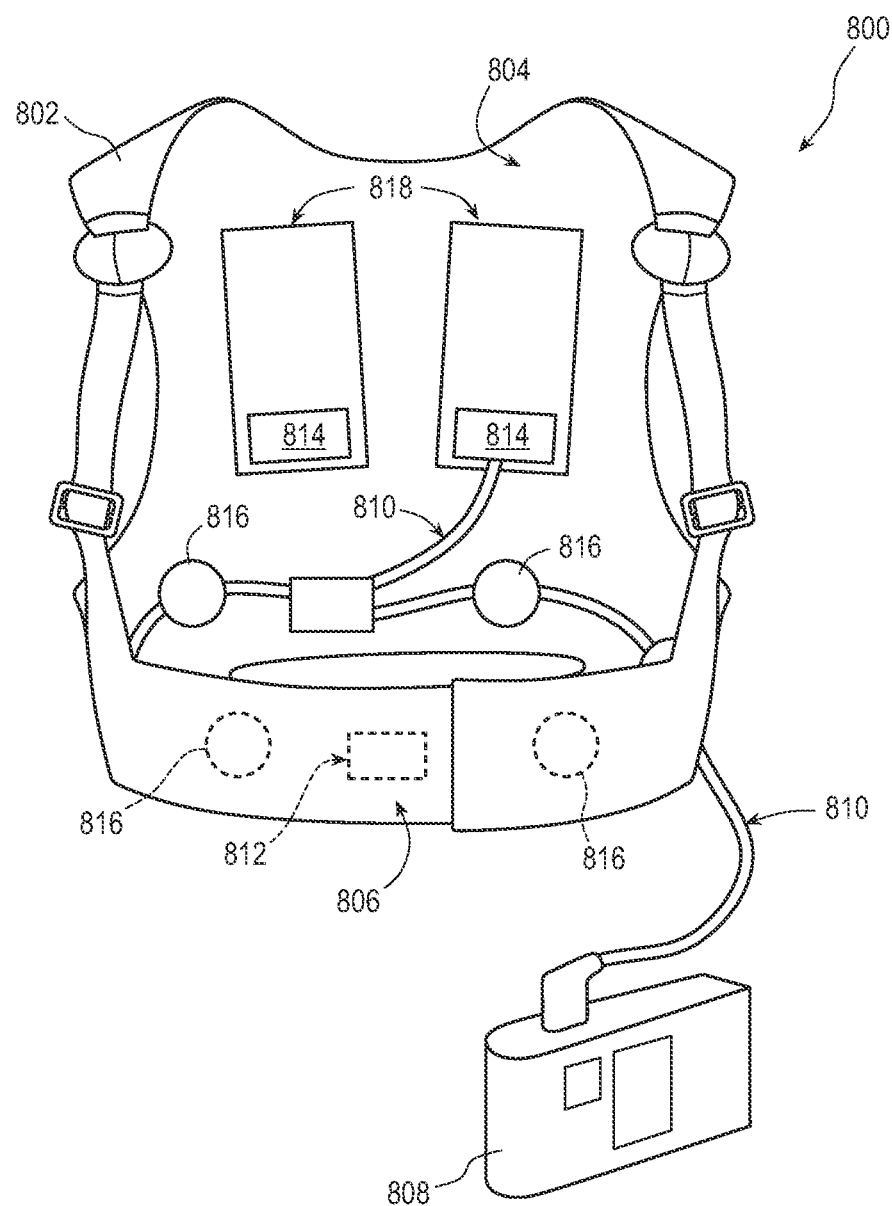
FIG. 8 is a diagram of sample embodiments of components of a wearable cardiac monitoring system in accordance with exemplary embodiments described herein.

FIG. 8 is a diagram of sample embodiments of components of a WCD system 800 according to exemplary embodiments. The cardiac device 804 may be an example of the cardiac device 604 describe with reference to FIG. 6. In some embodiments, the WCD system 800 may include a support structure 802 comprising a vest-like wearable garment. In some embodiments, the support structure 802 has a back side 804, and a front side 806 that closes in front of a chest of the patient.

In some embodiments, the WCD system 800 may also include an external defibrillator 808. The external defibrillator 808 may be an example of the defibrillator 608 describe with reference to FIGS. 6 and 7. As illustrated, FIG. 8 does not show any support for the external defibrillator 808, but as discussed, the defibrillator 808 may be carried in a purse, on a belt, by a strap over the shoulder, and the like as discussed previously. One or more wires 810 may connect the external defibrillator 808 to one or more electrodes 812, 814, 816. Of the connected electrodes, electrodes 812, 814 are defibrillation electrodes, and electrodes 816 are ECG sensing electrodes.

The support structure 802 is worn by the patient to maintain electrodes 812, 814, 816 on a body of the patient. For example, the back-defibrillation electrodes 814 are maintained in pockets 818. In some embodiments, the inside of the pockets 818 may comprise loose netting, so that the electrodes 814 can contact the back of the patient. In some instances, a conductive fluid may be deployed to increase connectivity. Additionally, in some embodiments, sensing electrodes 816 are maintained in positions that surround the patient's torso, for sensing ECG signals and/or the impedance of the patient.

In some instances, the ECG signals in a WCD system 800 may comprise too much electrical noise to be useful. To ameliorate the problem, multiple ECG sensing electrodes 816 are provided, for presenting many options to the processor (e.g., processor 202, FIG. 2). The multiple ECG sensing electrodes 816 provide different vectors for sensing the ECG signal of the patient.

Figure 9:
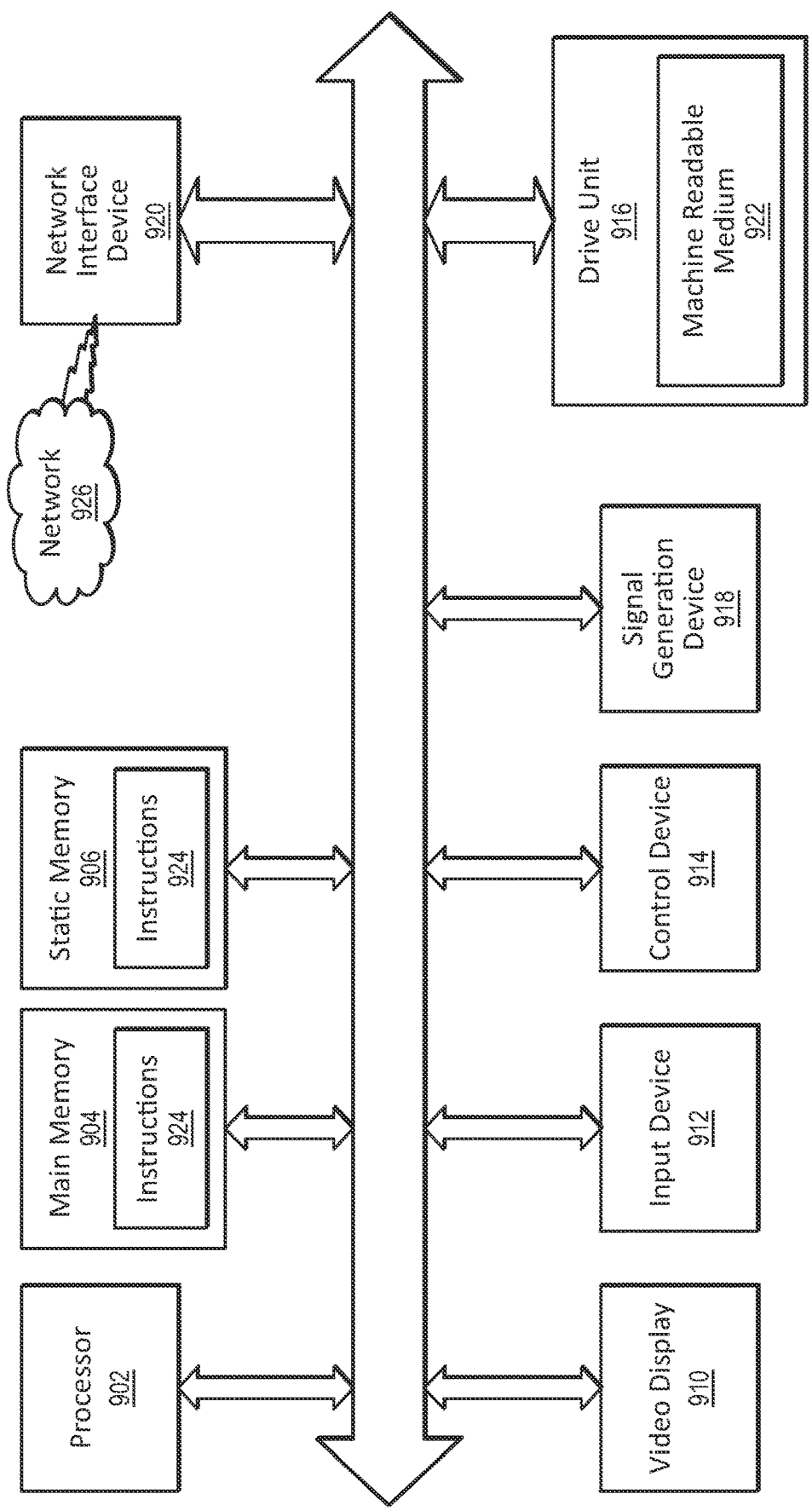
FIG. 9 is a block diagram of a sample components in accordance with exemplary embodiments described herein.

FIG. 9 is a diagram displaying various components of an example device 900. The device 900 may include a set of instructions causing the device 900 to perform any one or more of the methodologies described herein. In some embodiments, the device 900 may be an example of any of the devices described herein. In alternative embodiments, the device 900 may operate as a standalone device or may be connected (e.g., networked) to other machines. In a networked deployment, the device 900 may operate in the capacity of a server or a client machine in a server-client network environment or as a peer machine in a peer-to-peer (or distributed) network environment. The device 900 may be a server computer, a client computer, a personal computer (PC), a tablet PC, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single device 900 is illustrated, the term "machine" shall also be taken to include any collection of machines that individually or jointly execute a set (or multiple sets) of instructions to perform any one or more of the methodologies discussed herein.

The device 900 includes a processor 902 (e.g., a central processing unit (CPU), a graphics processing unit (GPU) or both), a main memory 904, and a static memory 906, which communicate with each other via a bus 908. The device 900 may further include a video display unit 910 (e.g., a liquid crystal display (LCD) or a cathode ray tube (CRT)). The device 900 also includes an alphanumeric input device 912 (e.g., a keyboard), a cursor control device 914 (e.g., a mouse), a disk drive unit 916, a signal generation device 918 (e.g., a speaker), and a network interface device 920.

The disk drive unit 916 includes a machine-readable medium 922 on which is stored one or more sets of instructions (e.g., software 924) embodying any one or more of the methodologies or functions described herein. The software 924 may also reside, completely or at least partially, within the main memory 904 and/or within the processor 902 during execution thereof by the device 900, the main memory 904, and the processor 902 also constituting machine-readable media. In alterative embodiments, software 924 may completely or partially reside within the static memory 904.

The software 924 may further be transmitted or received over a network 926 via the network interface device 920.

While the machine-readable medium 922 is shown in an example embodiment to be a single medium, the term "machine-readable medium" should be taken to include a single medium or multiple media (e.g., a centralized or distributed database and/or associated caches and servers) that store the one or more sets of instructions. The term "machine-readable medium" shall also be taken to include any medium that is capable of storing, encoding, or carrying a set of instructions for execution by the machine and that cause the machine to perform any one or more of the methodologies of the present invention. The term "machine-readable medium" shall accordingly be taken to include, but not be limited to, solid-state memories, optical and magnetic media, and carrier wave signals.

Figure 10:
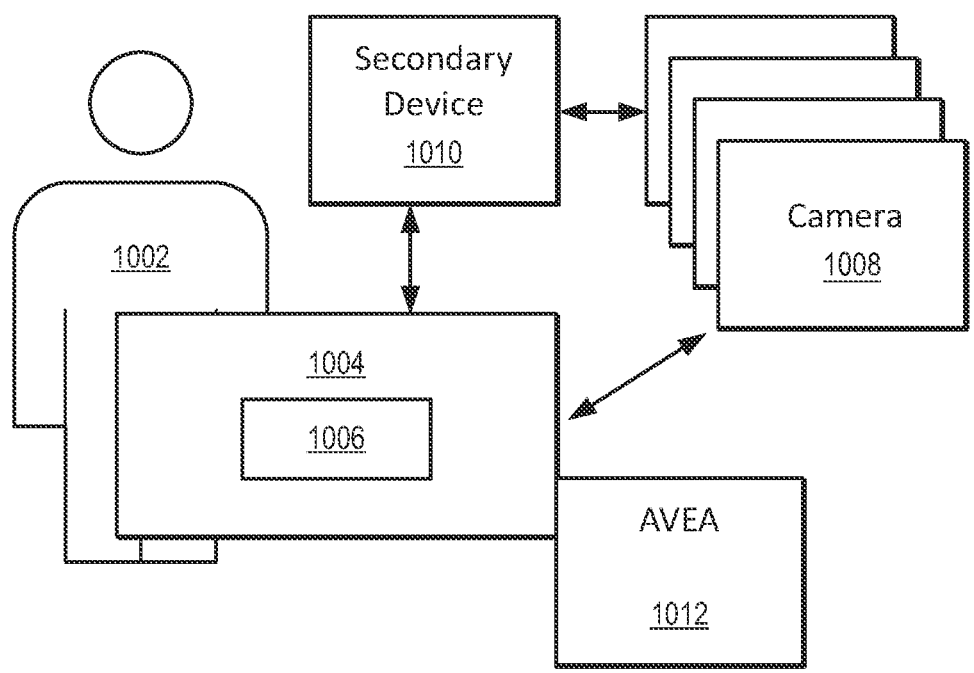
FIG. 10 is a diagram of sample embodiments of components of a wearable monitoring system in accordance with exemplary embodiments described herein.

FIG. 10 is a block diagram of a system 1000 to monitor a health of a patient. The system may include a patient 1002 with a wearable device 1004. The wearable device 1004 may include various cardiac devices. The wearable device 1004 may include one or more sensors 1006. In some embodiments, the wearable device may communicate with a secondary device 1010. The secondary device 1010 may comprise one or more mobile devices as described herein. In some embodiments, the wearable device 1004 may communicate with one or more cameras and an autonomous visual event assistant 1012.

In some embodiments, a wearable device 1004 may include a wearable cardioverter defibrillator (WCD), a smart watch, a wearable sensor device (e.g., glucose sensor, MCT or MCOT device, fitness tracker, etc.), and the like. The wearable device 1004 be positioned to detect when an emergency event involving the patient 1002 occurs. For example, if the wearable device 1004 is a WCD, the emergency event may be when the WCD has delivered a shock to the wearer. Other wearable devices 1004 may be configured to detect if the wearer is unconscious, or is not breathing, or cannot detect a pulse, or is not moving. For example, the wearable device 1004 may include a motion sensor 1006 such as an accelerometer configured to detect the wearer's movement, movement pattern, or lack of movement. The movement, movement pattern, or lack of movement can be compared to predetermined criteria to detect whether an emergency event has occurred. In some embodiments, the output of multiple sensors or wearable devices may be analyzed to determine whether an emergency event has occurred.

In some embodiments, the wearable device 1004 may include wireless communication circuitry (e.g., Bluetooth, NFC, Zigbee, etc.) to transmit signals to one or more cameras 1008 that are in proximity to the wearable device 1004. When an emergency event is detected, the wearable device 1004 may transmit a wireless signal or message to activate the one or more cameras 1008. In some embodiments, the wearable device 1002 may communicate with a separate communication device such as a secondary device 1010 such as a smartphone, tablet, etc. In some embodiments, the secondary device 1010 may include a camera which may be used to gain photographic data. In other embodiments, the secondary device 1010 may communicate with a remote camera 1008 proximate the wearable device 1004.

The one or more cameras 1008 can be set up in selected locations in which the patient 1002 may have an unwitnessed emergency event (e.g., locations around the residence of a patient's home, a patient's automobile, and the like). In some embodiments, the camera(s) 1008 may be part of a home or vehicle security system or both. The security system may be connected to the secondary device 1010, or the wearable device 1004, or both. In such embodiments, the security system may receive activation signals from the wearable device. In some embodiments, the wearable device 1004 and the camera(s) 1008 may include circuitry that allow the camera(s) 1008 to point and focus on the wearable device 1004. For example, the wearable device 1004 may emit a visual signal, audio signal, wireless signal, or some combination thereof which the camera(s) 1008 may detect for when activated by the wearable device 1004.

The one or more cameras 1008 may be video cameras or still cameras, with communication circuitry (wired and/or wireless) to transmit visual information to a remote location. In some embodiments, the cameras 1008 may transmit data to a Care Station (e.g., Care Station 112). For example, the one or more cameras 1008 may be connected via cable, DSL, fiber, Wi-Fi, cellular and/or other connection to a network such as the Internet. The camera(s) 1008 may transmit the data it captures to a predetermined remote location when activated by the wearable device 1004. In some embodiments, the remote location may be a care station data center, an emergency dispatch center, a server or call center operated by a non-governmental entity, for example: the company supplying the wearable device and/or cameras), a family member's computer or smartphone, doctor, or hospital facility, etc.

The visual information may provide appropriate personnel data to better assess the situation including the location of the wearer and what resources will be needed to respond to the emergency event. For example, in some embodiments, emergency dispatch personnel may determine which emergency personnel to dispatch, and which emergency equipment may be necessary. In some embodiments, the cameras 1008 may enable the emergency dispatcher to assess the area around the patient 1002 for other bystanders that might aid the patient 1002. In some embodiments, the camera(s) 1008 may include a user interface (e.g., audio speakers, a display or projector, microphone, a keyboard, etc.) to enable communication between bystanders and the emergency dispatcher. For example, the dispatcher can provide CPR instructions to the bystander if needed.

In one example, the wearable device 1004 may include a WCD. The WCD may send an activation signal to a nearby camera 1008 when an emergency event is detected. In some other embodiments, the WCD may send an activation signal to a secondary device 1010 paired with the WCD, which in turn sends an activation signal to the nearby camera(s) 1008. In some embodiments, the data may also be sent to a remote location such as a care station (e.g., care station 112).

In some embodiments, if the wearable device 1004 has detected an unshockable arrhythmia, the wearable device 1004 may analyze data from other one or more other sensors proximate the wearable device 1004 to determine if an emergency event has occurred. For example, in some embodiments, the wearable device 1004 may include a motion sensor to detect the patient's movement, movement pattern, or lack of movement. The wearable device 1004 may analyze the data to determine if any data indicates predetermined criteria which may indicate an event has occurred. In some embodiments, the predetermined criteria may include one or more of the following: an indication that the patient is wearing the wearable device 1004 (e.g., the device 1004 may detect transthoracic impedance, patient temperature, movement, or the like); a lack of movement for a predetermined time period; a sudden acceleration immediately preceding the lack of movement (which can indicate the patient has fallen), etc. If the movement, movement pattern, or lack of movement data meet predetermined criteria, the wearable device 1004 may analyze the data in conjunction with the unshockable arrhythmia to corroborate an emergency event for which the wearable device 1004 should send an activation signal to the camera(s) and/or remote location. In some embodiments, the data may disprove an emergency event, which may lead to less immediate reactions. For example, the wearable device 1004 may request patient input or continue to detect motion data to determine if the patient is still functional.

In other embodiments, the wearable device 1004 may use motion sensor data alone to determine when an emergency event occurs. For example, the wearable device 1004 may detect movement data which may indicate a loss of consciousness due to asystole, bradycardia, low glucose level, syncope, etc. Such a sudden movement may cause the wearable device 1004 to send an activation signal to the camera(s) 1008 and/or a remote location.

In some embodiments, the wearable device 1004 may monitor a user interface for a user response before sending the activation signal to the camera(s) 1008. For example, the wearable device 1004 may send an alert or prompt to the patient 1002 to input a response via the user interface to cancel the emergency event alert. If the patient 1002 responds within a predetermined time period of the alert, the wearable device 1004 does not send the activation signal to the camera(s) 1008. In contrast, if the wearer does not respond within the time period, the wearable device 1008 sends the activation signal to the camera(s) 1008 and/or to the remote location (e.g., care station 112). In some embodiments, the remote location may take one or more emergency responses including contacting emergency personnel.

In a further example, the visual of the scene can be also transmitted to a caregiver, medical doctor, or family member to help them in locating the patient and in providing assistance. For example, the system 1000 may aid the patient 1002 when the patient requires assistance. The wearable device 1004, the camera(s) 1008, the secondary device 1010, or some combination thereof may transmit information to emergency personnel. The information may include one or more of a time stamp, location, and potentially other helpful information, such as for example how to access the house. In a further example, in some embodiments, the system or person at the remote location may receive camera data of the premises entry and can remotely unlock the premises entry in response to recognizing a responder(s) or in response to a communication from the responder(s).

In some embodiments, the system 1000 may notify designated emergency contacts and provide location updates after the patient 1002 has been taken from the emergency scene. For example, the system can include a notification system as disclosed in U.S. Patent Publication No. 2018/0221645 entitled "WEARABLE CARDIAC DEFIBRILLATOR SYSTEMS & METHODS & SOFTWARE FOR CONTACTING NON-WITNESSING RESPONDERS", which is incorporated herein by reference in its entirety for all purposes. In addition, if emergency responders take the patient 1002 to a particular hospital while the patient is still wearing the wearable device 1004, the wearable device 1004 may provide updates of its location to the designated individuals.

In some embodiments, the system 1000 may include an autonomous visual event assistant (AVEA) 1012 coupled to a charging station (not shown) for the wearable device 1004. In some embodiments, the AVEA 1012 is implemented as disclosed U.S. Provisional Application No. 63/069,638 filed Aug. 24, 2020, entitled "Autonomous Visual Event Assistant (AVEA)", which is incorporated by reference herein it its entirety for all purposes. As disclosed in U.S. Prov. App. No. 63/069,638, an AVEA 1012 can be configured to fly, move around, move from place to place, hover, and convey visual and/or auditory information about a person or a scene, upon activation.

As mentioned above, the wearable device 1004 may be a WCD system. The WCD system may include a charging station for charging a battery of the WCD, which may also be used to charge the AVEA 1012.

In some embodiments, the AVEA 1012 may replace the cameras 1008 or act in conjunction with the cameras 1008. For example, the wearable device 1004 may activate the AVEA 1012 when an emergency event is detected. The AVEA 1012 may launch, navigate to the patient 1002, and activate one or more cameras proximate the AVEA 1012. In some embodiments, the AVEA 1012 may provide visual information to a remote location as discussed previously. In some embodiments, the AVEA 1012 does not information. Rather, the AVEA 1012 may stream images, video, sound, or some combination thereof to a remote location. In other embodiments, the AVEA can store select data such as time it was triggered, duration of the event and/or one or more events. In some embodiments, the AVEA 1012 may convey GPS coordinates of the event. In some embodiments, the AVEA 1012 may integrate with home or personal security systems and can be activated based on information from other environmental sensors, such as carbon monoxide, house motion sensors, etc., and can be programmed to contact designated individuals or rescue.

Figure 11:
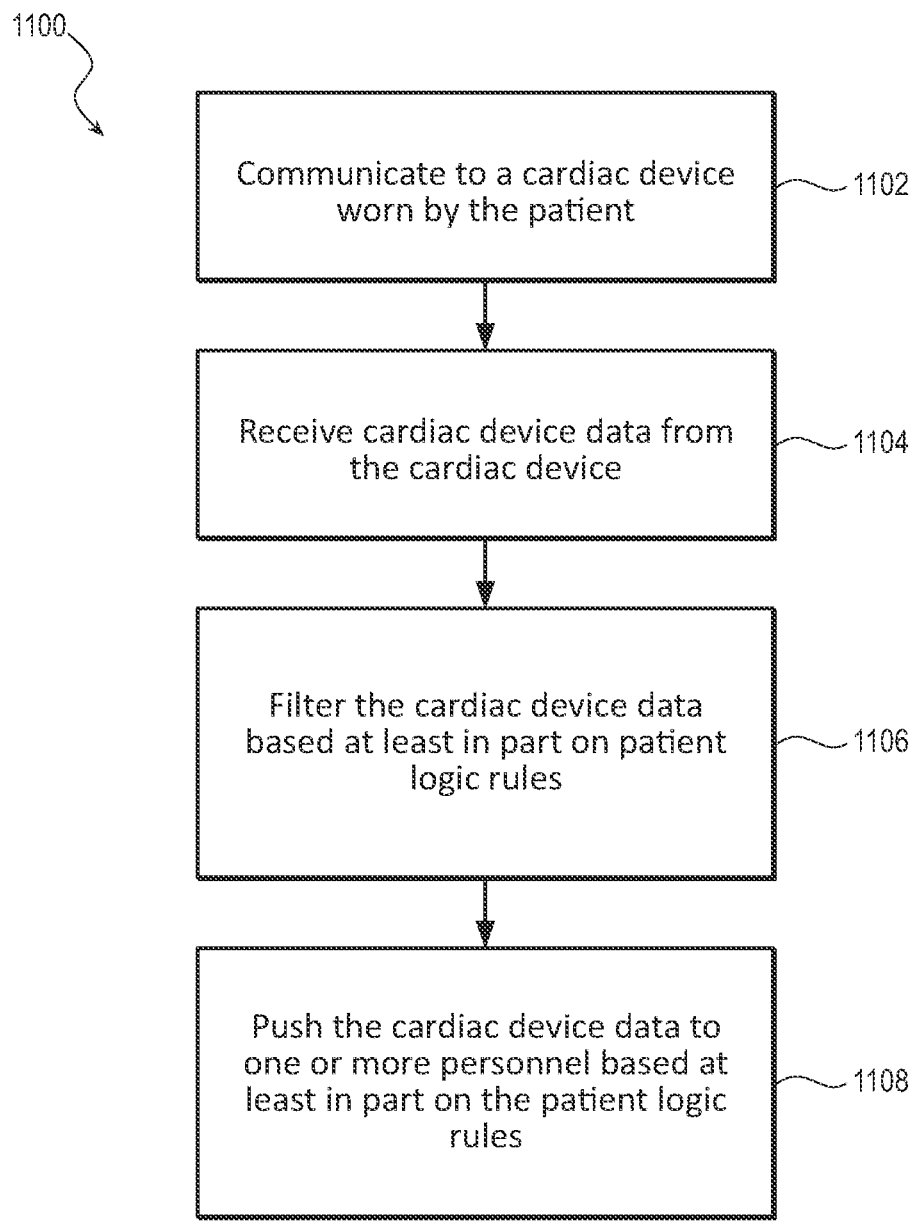
FIG. 11 is a flow diagram in accordance with exemplary embodiments described herein.

FIG. 11 is a flow chart illustrating an example of a method 1100 for cardiac device systems, in accordance with various aspects of the present disclosure. For clarity, the method 1100 is described below with reference to aspects of one or more of the systems described herein.

At block 1102, the method 1100 may communicate to a cardiac device worn by the patient. For example, a mobile device may establish a connection with a wearable device. The wearable device may be a cardiac device. In some embodiments, the device may include a WCD.

At block 1104, the method 1100 may receive cardiac information from the cardiac device. For example, the cardiac device may be worn by the patient and include at least one sensor. The cardiac device may detect vital signs from the patient include a heart rate. The cardiac device may then push that data to a mobile device. The data may be raw unfiltered data or may be filtered data. In some embodiments, the cardiac device may push the data to the mobile device at predetermined intervals. In other embodiments, the cardiac device may only push data when an anomaly is detected. In still further embodiments, the mobile device may request data. For example, the mobile device may ping the cardiac device for data at predetermined intervals. In other embodiments, the mobile device may be triggered by a third party to collect the data.

At block 1106, the method 1100 may filter the cardiac data based at least in part on patient logic rules. For example, the method 1100 may distribute the data to multiple parties. Each party may be privy to select bits of information. The method 1100 may have a series of rules for each separate party and may filter data through the rules prior to distributing data. For example, a device customer service rep may not need the patient's heart rate data whereas medical personnel may not need device data. The patient logic rules ensure each party receives only the data necessary and compliant with rules and regulations.

At block 1108, the method 1100 may push the cardiac device data to one or more personnel based at least in part on the patient logic rules. For example, once the data has been filtered, the method 1100 may distribute the appropriate data to each party. In some embodiments, if a party is requesting data, such as medical personnel, the method 1100 may only distribute data to the requesting party. In other embodiments, the method 1100 may distribute data on predetermined schedule to each party. In still further embodiments, the method 1100 may distribute data when an issue occurs. The issue may include a cardiac event or an equipment issue.

Thus, the method 1100 may provide for one method of monitoring a patient's cardiac health and well-being. It should be noted that the method 1100 is just one implementation and that the operations of the method 1100 may be rearranged or otherwise modified such that other implementations are possible.

Figure 12:
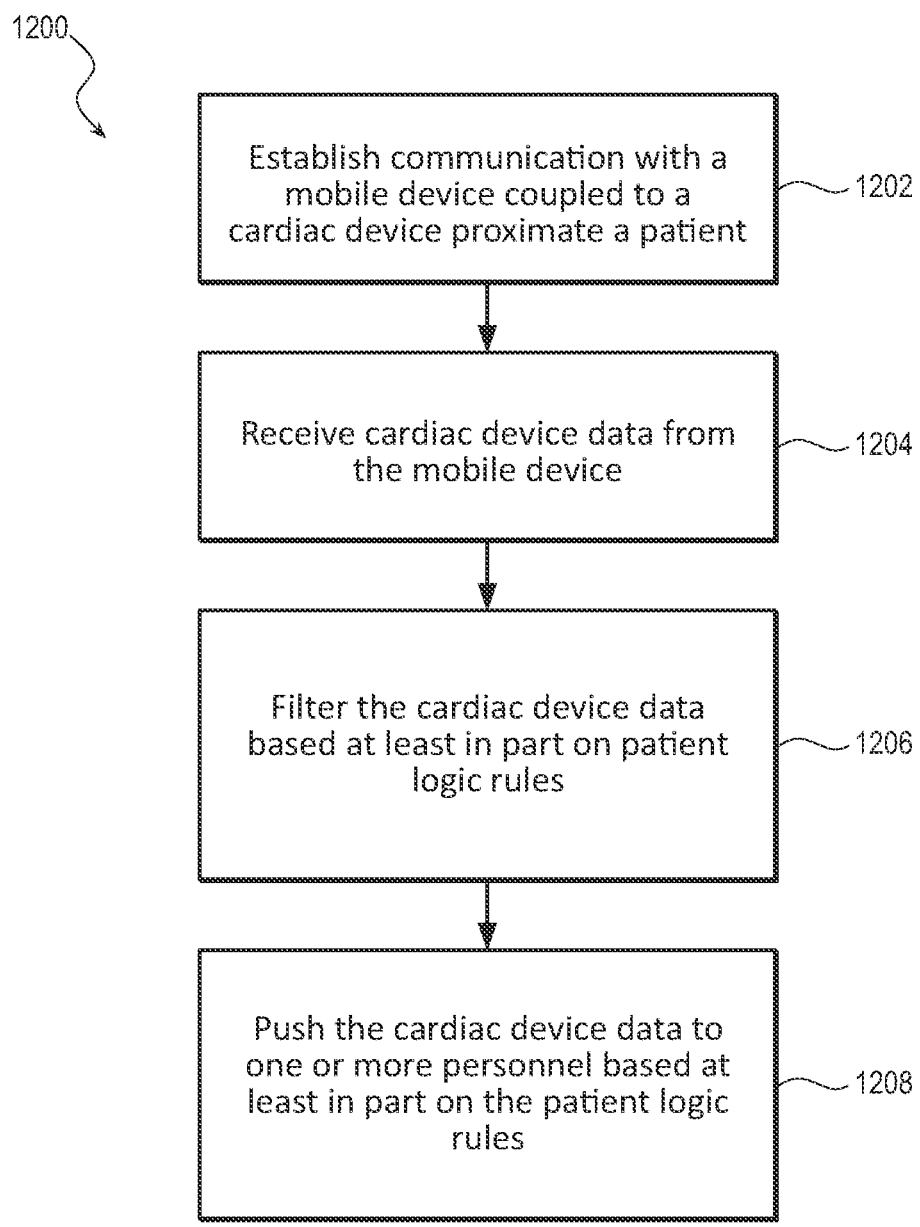
FIG. 12 is a flow diagram in accordance with exemplary embodiments described herein

FIG. 12 is a flow chart illustrating an example of a method 1200 for cardiac device systems, in accordance with various aspects of the present disclosure. For clarity, the method 1200 is described below with reference to aspects of one or more of the systems described herein.

At block 1202, the method 1200 may establish communication with a mobile device coupled to a cardiac device worn by the patient. For example, a mobile device may establish a connection with a wearable device. The wearable device may be a cardiac device. In some embodiments, the device may include a WCD. The mobile device may be a unique device capable of internet transmissions or may be a patient's own mobile device with a data plan or capable of transmitting data over WiFi.

At block 1204, the method 1200 may receive cardiac information from the cardiac device. For example, the method 1200 may ping the mobile device for data. In some embodiments, the mobile device may be readily receiving data in real time from the wearable device. In other embodiments, the mobile device may either be requesting or receiving data at predetermined time periods. The method 1200 may, from a server, ping the mobile device for data. The request for data may include only the most recent data stored by the mobile device. In other embodiments, the request may be for more real-time data and the mobile device may need to request data from the cardiac device.

For example, the cardiac device may be worn by the patient and include at least one sensor. The cardiac device may detect vital signs from the patient include a heart rate. The cardiac device may then push that data to a mobile device. The data may be raw unfiltered data or may be filtered data. In some embodiments, the cardiac device may push the data to the mobile device at predetermined intervals. In other embodiments, the cardiac device may only push data when an anomaly is detected. In still further embodiments, the mobile device may request data. For example, the mobile device may ping the cardiac device for data at predetermined intervals. In other embodiments, the mobile device may be triggered by a third party to collect the data. For example, a third party may request the data which may trigger the server to ping the wearable device.

At block 1206, the method 1200 may filter the cardiac data based at least in part on patient logic rules. For example, the method 1200 may distribute the data to multiple parties. Each party may be privy to select bits of information. The method 1200 may have a series of rules for each separate party and may filter data through the rules prior to distributing data. For example, a device customer service rep may not need the patient's heart rate data whereas medical personnel may not need device data. The patient logic rules ensure each party receives only the data necessary and compliant with rules and regulations.

At block 1208, the method 1200 may push the cardiac device data to one or more personnel based at least in part on the patient logic rules. For example, once the data has been filtered, the method 1200 may distribute the appropriate data to each party. In some embodiments, if a party is requesting data, such as medical personnel, the method 1200 may only distribute data to the requesting party. In other embodiments, the method 1200 may distribute data on predetermined schedule to each party. In still further embodiments, the method 1200 may distribute data when an issue occurs. The issue may include a cardiac event or an equipment issue.

Thus, the method 1200 may provide for one method of monitoring a patient's cardiac health and well-being. It should be noted that the method 1200 is just one implementation and that the operations of the method 1200 may be rearranged or otherwise modified such that other implementations are possible.

Figure 13:
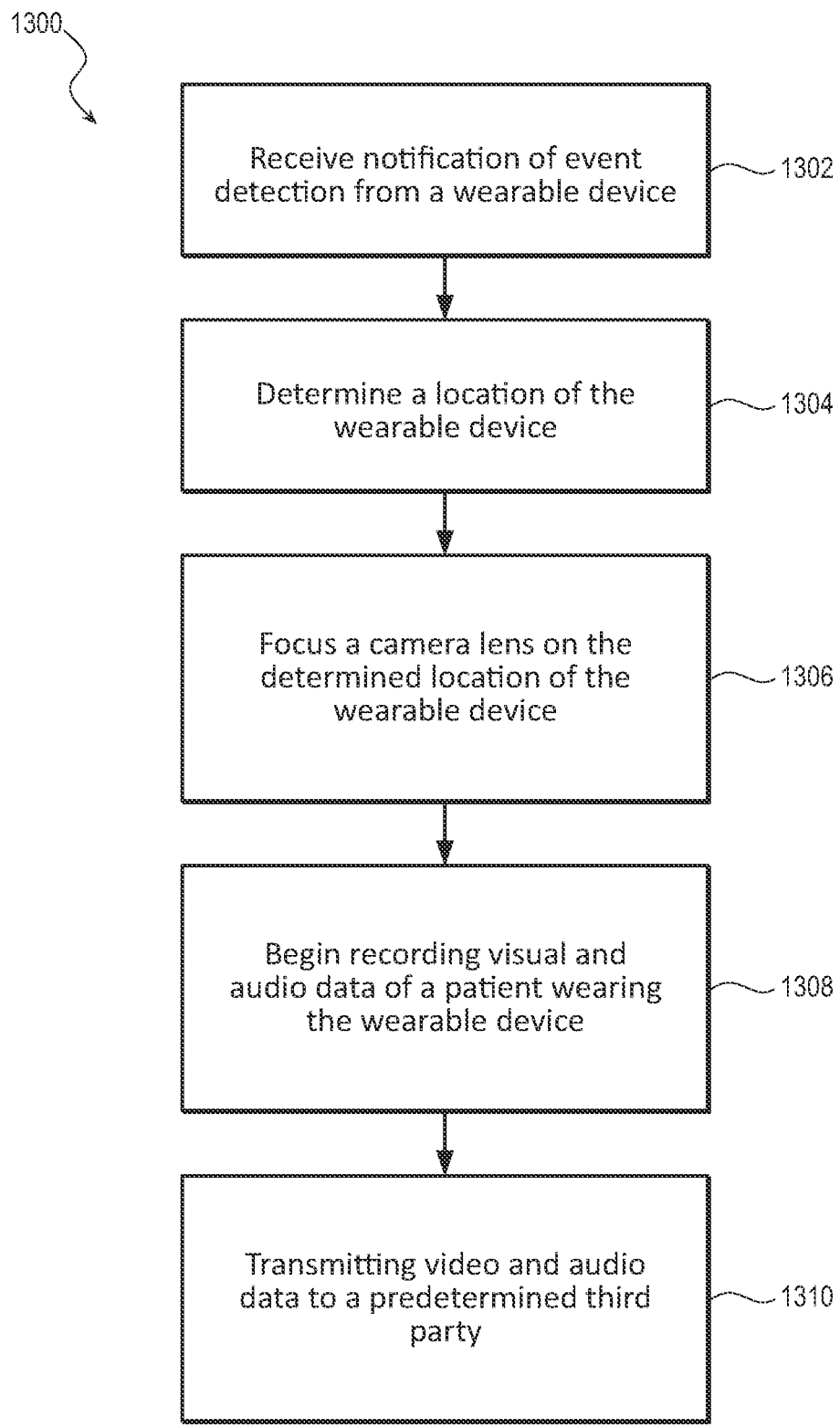
FIG. 13 is a flow diagram in accordance with exemplary embodiments described herein.

FIG. 13 is a flow chart illustrating an example of a method 1300 for cardiac device systems, in accordance with various aspects of the present disclosure. For clarity, the method 1300 is described below with reference to aspects of one or more of the systems described herein.

At block 1302, the method 1300 may receive a notification of an event detection from a wearable device. The patient may be wearing a wearable device which may detect heart conditions. For example, the wearable device may detect a cardiac event. The patient may be experiencing an irregular heartbeat. In some embodiments, the patient may be experiencing a heart attack. The wearable device may also detect numerous other cardiac anomalies.

At block 1304, the method 1300 may determine a location of the wearable device. For example, in some embodiments, either the wearable device or a mobile device communicatively coupled to the wearable device may transmit a location. The location may be GPS coordinates or may comprise a more mundane description, such as "bedroom."

At block 1306, the method 1300 may focus a camera lens on the determined location of the wearable device. For example, in some embodiments, one or more stationary cameras may be positioned around a patient's environment. The method 1300 may communicate with the cameras. For example, in some embodiments, the cameras may be part of the cardiac monitoring system or may be part of a home alarm system capable of communicating with the wearable device. In still further embodiments, the camera may be a part of the AVEA system, which may travel to a location associated with the wearable device and therefore the patient.

At block 1308, the method 1300 may begin recording visual and audio data of a patient wearing the wearable device. Once the camera is either activated or in the location of the patient, the camera may begin capturing data. The data may include an image of the patient and their surroundings.

At block 1310, the method 1300 may transmit the video and audio data to a predetermined third party. In some embodiments, the camera itself, either through its own system such as the security system, or through the AVEA system, may transmit data to a server associated with the wearable device. The server may begin to store and analyze the data.

In some embodiments, if the patient is experiencing a cardiac event, the method 1300 may activate a speaker proximate the patient. The speaker may be a part of the camera or AVEA system. In still further embodiments, the speaker may be a part of the wearable device of the mobile device associate with the patient. The speaker may prompt the patient to take one or more actions or may attempt to wake or gain the attention of the patient.

If the system 1300 detects a nearby person in the video or audio data, the method 1300 may attempt to prompt the person to aid in the patient's emergency response.

Thus, the method 1300 may provide for one method of monitoring a patient's cardiac health and well-being. It should be noted that the method 1300 is just one implementation and that the operations of the method 1300 may be rearranged or otherwise modified such that other implementations are possible.

A person skilled in the art will be able to practice the present invention after careful review of this description, which is to be taken as a whole. Details have been included to provide a thorough understanding. In other instances, well-known aspects have not been described, in order to not obscure unnecessarily this description.

Some technologies or techniques described in this document may be known. Even then, however, it is not known to apply such technologies or techniques as described in this document, or for the purposes described in this document.

This description includes one or more examples, but this fact does not limit how the invention may be practiced. Indeed, examples, instances, versions or embodiments of the invention may be practiced according to what is described, or yet differently, and also in conjunction with other present or future technologies. Other such embodiments include combinations and sub-combinations of features described herein, including for example, embodiments that are equivalent to the following: providing or applying a feature in a different order than in a described embodiment; extracting an individual feature from one embodiment and inserting such feature into another embodiment; removing one or more features from an embodiment; or both removing a feature from an embodiment and adding a feature extracted from another embodiment, while providing the features incorporated in such combinations and sub-combinations.

In general, the present disclosure reflects preferred embodiments of the invention. The attentive reader will note, however, that some aspects of the disclosed embodiments extend beyond the scope of the claims. To the respect that the disclosed embodiments indeed extend beyond the scope of the claims, the disclosed embodiments are to be considered supplementary background information and do not constitute definitions of the claimed invention.

In this document, the phrases "constructed to", "adapted to" and/or "configured to" denote one or more actual states of construction, adaptation and/or configuration that is fundamentally tied to physical characteristics of the element or feature preceding these phrases and, as such, reach well beyond merely describing an intended use. Any such elements or features can be implemented in a number of ways, as will be apparent to a person skilled in the art after reviewing the present disclosure, beyond any examples shown in this document.

Incorporation by reference: References and citations to other documents, such as patents, patent applications, patent publications, journals, books, papers, web contents, have been made throughout this disclosure. All such documents are hereby incorporated herein by reference in their entirety for all purposes.

Parent patent applications: Any and all parent, grandparent, great-grandparent, etc. patent applications, whether mentioned in this document or in an Application Data Sheet ("ADS") of this patent application, are hereby incorporated by reference herein as originally disclosed, including any priority claims made in those applications and any material incorporated by reference, to the extent such subject matter is not inconsistent herewith.

Reference numerals: In this description a single reference numeral may be used consistently to denote a single item, aspect, component, or process. Moreover, a further effort may have been made in the preparation of this description to use similar though not identical reference numerals to denote other versions or embodiments of an item, aspect, component or process that are identical or at least similar or related. Where made, such a further effort was not required, but was nevertheless made gratuitously so as to accelerate comprehension by the reader. Even where made in this document, such a further effort might not have been made completely consistently for all of the versions or embodiments that are made possible by this description. Accordingly, the description controls in defining an item, aspect, component or process, rather than its reference numeral. Any similarity in reference numerals may be used to infer a similarity in the text, but not to confuse aspects where the text or other context indicates otherwise.

The claims of this document define certain combinations and sub combinations of elements, features and acts or operations, which are regarded as novel and non-obvious. The claims also include elements, features and acts or operations that are equivalent to what is explicitly mentioned. Additional claims for other such combinations and sub combinations may be presented in this or a related document. These claims are intended to encompass within their scope all changes and modifications that are within the true spirit and scope of the subject matter described herein. The terms used herein, including in the claims, are generally intended as "open" terms. For example, the term "including" should be interpreted as "including but not limited to," the term "having" should be interpreted as "having at least," etc. If a specific number is ascribed to a claim recitation, this number is a minimum but not a maximum unless stated otherwise. For example, where a claim recites "a" component or "an" item, it means that the claim can have one or more of this component or this item.

Other embodiments include combinations and sub-combinations of features described or shown in the drawings herein, including for example, embodiments that are equivalent to: providing or applying a feature in a different order than in a described embodiment, extracting an individual feature from one embodiment and inserting such feature into another embodiment; removing one or more features from an embodiment; or both removing one or more features from an embodiment and adding one or more features extracted from one or more other embodiments, while providing the advantages of the features incorporated in such combinations and sub-combinations. As used in this paragraph, feature or features can refer to the structures and/or functions of an apparatus, article of manufacture or system, and/or the steps, acts, or modalities of a method.

In construing the claims of this document, the inventor(s) invoke 35 U.S.C. § 112(f) only when the words "means for" or "steps for" are expressly used in the claims. Accordingly, if these words are not used in a claim, then that claim is not intended to be construed by the inventor(s) in accordance with 35 U.S.C. § 112(f).

What is claimed is:

1. A method to track cardiac health of a patient, the method comprising:
   communicating, via a mobile device, to a cardiac device worn by the patient, wherein the cardiac device includes at least one sensor;
   receiving cardiac device data from the cardiac device;
   filtering the cardiac device data based, at least in part, on patient logic rules, wherein the patient logic rules comprise rules to restrict and grant access to portions of the cardiac device data; and
   pushing the filtered cardiac device data to one or more personnel based, at least in part, on the patient logic rules.

2. The method of claim 1, further comprising:
   issuing a notification to the one or more personnel.

3. The method of claim 1, further comprising:
   detecting a voice command;
   interpreting the voice command; and
   taking one or more actions concerning the cardiac device based, at least in part, on the interpreted voice command.

4. The method of claim 1, wherein the cardiac device is a wearable cardiac defibrillator.

5. The method of claim 1, further comprising:
   mirroring the cardiac device data on a second device remote from the mobile device, wherein the second device is associated with professional personnel.

6. The method of claim 5, wherein the cardiac device data is filtered and approved for the professional personnel.

7. The method of claim 6, further comprising:
   receiving a message from the professional personnel; and
   displaying the received message to the patient.

8. A method to track cardiac health of a patient, the method comprising:
   establishing communication with a mobile device coupled to a cardiac device proximate the patient, wherein the cardiac device includes at least one sensor;
   receiving cardiac device data from the mobile device;
   filtering the cardiac device data based, at least in part, on patient logic rules, wherein the patient logic rules comprise rules to restrict and grant access to portions of the cardiac device data; and
   pushing the filtered cardiac device data to one or more personnel based, at least in part, on the patient logic rules.

9. The method of claim 8, further comprising:
   issuing a notification to one or more health care personnel, wherein the notification includes a health alert about the patient.

10. The method of claim 8, further comprising:
    transferring patient health data and identification information to one or more health care personnel based, at least in part, on the patient logic rules.

11. The method of claim 8, wherein the cardiac device is a wearable cardiac defibrillator.

12. The method of claim 8, further comprising:
    removing patient identifying information from patient health data; and
    transferring anonymous patient health data to one or more providers of the cardiac device based, at least in part, on the patient logic rules.

13. The method of claim 8, further comprising:
    removing patient identifying information from patient health data and device data; and
    transferring anonymous patient health data and device data to one or more customer service personnel based, at least in part, on the patient logic rules.

14. The method of claim 8, wherein the patient logic rules are implemented using at least one of a care station logic module, a medical logic module, a customer service logic module, and a customer relationship management (CRM) logic module.

15. The method of claim 14, wherein the care station logic module filters the cardiac device data for storage at a centralized location.

16. The method of claim 15, wherein the care station logic module is a centralized storage database that runs the patient logic rules.

17. The method of claim 14, wherein the medical logic module filters data for transferring to medical personnel.

18. The method of claim 14, wherein the customer service logic module filters device data for customer service personnel.

19. The method of claim 14, wherein the CRM logic module filters patient data for CRM personnel.

* * * * *